United States Patent
Imai et al.

(10) Patent No.: US 11,867,691 B2
(45) Date of Patent: *Jan. 9, 2024

(54) IMAGE PROCESSING DEVICE, ANALYSIS DEVICE, IMAGE PROCESSING METHOD, IMAGE PROCESSING PROGRAM, AND DISPLAY DEVICE

(71) Applicants: NIKON CORPORATION, Tokyo (JP); The University of Tokyo, Tokyo (JP)

(72) Inventors: Kenta Imai, Chigasaki (JP); Mamiko Masutani, Yokohama (JP); Masayuki Murata, Tokyo (JP); Fumi Kano, Tokyo (JP); Yoshiyuki Noguchi, Tokyo (JP)

(73) Assignees: NIKON CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 1046 days.

This patent is subject to a terminal disclaimer.

(21) Appl. No.: 16/481,803

(22) PCT Filed: Feb. 3, 2017

(86) PCT No.: PCT/JP2017/003947
§ 371 (c)(1),
(2) Date: Jul. 29, 2019

(87) PCT Pub. No.: WO2018/142570
PCT Pub. Date: Aug. 9, 2018

(65) Prior Publication Data
US 2019/0376952 A1    Dec. 12, 2019

(51) Int. Cl.
G01N 31/00 (2006.01)
G01N 33/53 (2006.01)
G01N 33/50 (2006.01)

(52) U.S. Cl.
CPC ................ G01N 33/5044 (2013.01)

(58) Field of Classification Search
None
See application file for complete search history.

(56) References Cited

U.S. PATENT DOCUMENTS

| | | | | |
|---|---|---|---|---|
| 7,920,327 | B2* | 4/2011 | Ohata | G02B 15/177 |
| | | | | 359/713 |
| 9,280,698 | B2 | 3/2016 | Kll et al. | |
| 11,321,836 | B2* | 5/2022 | Masutani | G06T 7/0012 |
| 2017/0350805 | A1 | 12/2017 | Murata et al. | |

FOREIGN PATENT DOCUMENTS

| | | | | |
|---|---|---|---|---|
| JP | 2011-229410 A | 11/2011 | | |
| JP | 2016-123366 A | 7/2016 | | |
| WO | 2014/049580 A2 | 4/2014 | | |
| WO | WO-2014049580 A2 * | 4/2014 | ......... | C12N 15/1086 |
| WO | WO-2014093838 A2 * | 6/2014 | .......... | G01N 21/253 |
| WO | 2016/103501 A1 | 6/2016 | | |

OTHER PUBLICATIONS

Kissova et al. (Autophagy, 2007, vol. 3, No. 4, p. 329-336) (Year: 2007).*
Morikawa, Takamitsu et al."Dependence of Fluorescent Protein Brightness on Protein Concentration in Solution and Enhancement of it". Scientific Reports 6, Article No. 22342, pp. 1-13, 2016.
Friedman, Jerome et al. "Sparse Inverse Covariance Estimation With The Graphical Lasso". Biostatistics, 9, 3, pp. 432-441, 2008.
Kissova, Ingrid et al. "Selective and Non-Selective Autophagic Degradation of Mitochondria in Yeast". Autophagy, vol. 3, No. 4, pp. 329-336, 2007.
May 9, 2017 International Search Report issued in International Application No. PCT/JP2017/003947.
May 9, 2017 Written Opinion issued in International Application No. PCT/JP2017/003947.
Mar. 17, 2020 Office Action issued in Japanese Patent Application No. 2018-565194.

* cited by examiner

*Primary Examiner* — Lisa V Cook
(74) *Attorney, Agent, or Firm* — Oliff PLC

(57) ABSTRACT

An image processing device includes a determination unit configured to determine a type of autophagy induced in a cell, based on information indicative of autophagic activity in the cell present in a cell image in which the cell is image captured and based on information indicative of congestion of molecules in the cell present in the cell image.

16 Claims, 15 Drawing Sheets

(A-1)

(A-2)

(B-1)

(B-2)

IMAGE PROCESSING DEVICE, ANALYSIS DEVICE, IMAGE PROCESSING METHOD, IMAGE PROCESSING PROGRAM, AND DISPLAY DEVICE

TECHNICAL FIELD

The present invention relates to an image processing device, an analysis device, an image processing method, an image processing program, and a display device.

BACKGROUND ART

In biological science, medical science, and the like, it is known that there is a correlation between a state of an organism such as health and a disease and, for example, a state of cell(s), organelles in the cell(s), and the like. Thus, analyzing the correlation between these is one technique for solving various issues in biological science, medical science, and the like. In addition, for example, analyzing signaling pathways of information transmitted between cells or within cell(s) can be helpful for research relating to biosensors in industrial applications, in the manufacture of drugs with the aim of preventing a disease, and the like. In various analysis techniques relating to cell(s) and tissue slices, techniques using image processing are known, for example (see Patent Document 1, for example).

CITATION LIST

Patent Literature

Patent Document 1: U.S. Pat. No. 9,280,698

SUMMARY OF INVENTION

A first aspect of the present invention provides an image processing device including a determination unit configured to determine a type of autophagy induced in a cell, based on information indicative of autophagic activity in a cell present in a cell image in which the cell is image captured and based on information indicative of congestion of molecules in the cell present in the cell image.

A second aspect of the present invention provides an analysis device including a feature value calculation unit configured to calculate a feature value of a subcellular component, based on a cell image in which the cell is image captured; a function estimation unit configured to estimate a function of the cell; and a function correlation calculation unit configured to calculate a correlation between the function of the cell estimated by the function estimation unit and the feature value of the subcellular component.

A third aspect of the present invention provides an image processing method including a determining step of determining a type of autophagy induced in a cell, based on information indicative of autophagic activity in the cell present in a cell image in which the cell is image captured and based on information indicative of congestion of molecules in the cell present in the cell image.

A fourth aspect of the present invention provides an image processing program causing a computer to execute a determining step of determining a type of autophagy induced in a cell, based on information indicative of autophagic activity in the cell present in a cell image in which the cell is image captured and based on information indicative of congestion of molecules in the cell present in the cell image.

A fifth aspect of the present invention provides a display device including a display unit configured to display a determination result acquired from a determination unit configured to determine a type of autophagy induced in a cell, based on information indicative of autophagic activity in the cell present in a cell image in which the cell is image captured and based on information indicative of congestion of molecules in the cell present in the cell image.

DESCRIPTION OF EMBODIMENTS

First Embodiment

Figure 1:
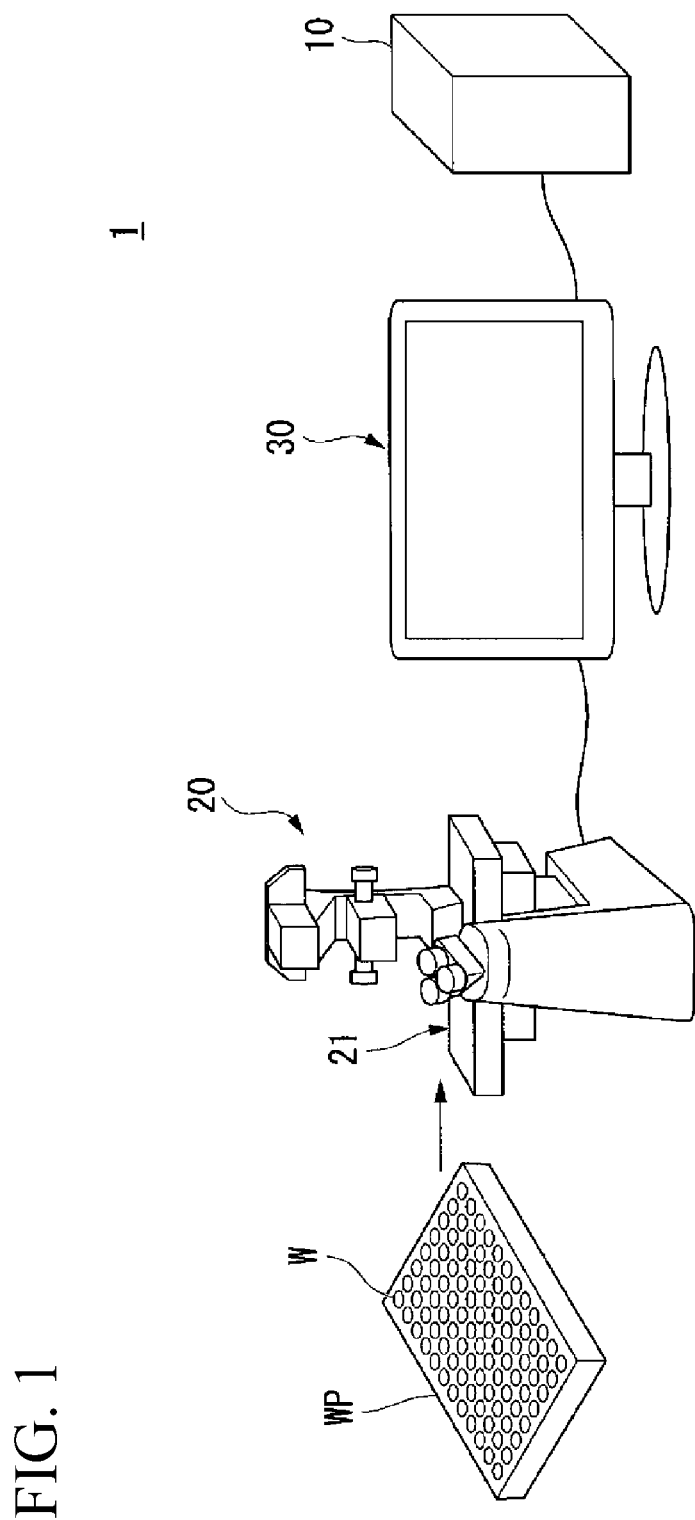
FIG. 1 is a view illustrating a configuration example of a microscope observation system.

An embodiment according to the present invention will be described below with reference to the drawings. FIG. 1 is a view illustrating a configuration example of a microscope observation system 1 according to an embodiment of the present invention.

The microscope observation system 1 performs image processing on an image acquired by image capturing cell(s) and the like. In the following description, the image acquired by image capturing cell(s) or the like is also simply referred to as a cell image.

The microscope observation system 1 includes an image processing device 10, a microscope apparatus 20, and a display unit 30.

The microscope apparatus 20 is a biological microscope and includes an electromotive stage 21 and an image capturing unit 22. The electromotive stage 21 can arbitrarily move a position of an imaging target in a predetermined direction (for example, in a certain direction within a two-dimensional plane in a horizontal direction).

The image capturing unit 22 includes an imaging element such as a Charge-Coupled Device (CCD) and a Complementary Metal-Oxide Semiconductor (CMOS), and is configured to image capture the imaging target on the electromotive stage 21. Note that the microscope apparatus 20 may not include the electromotive stage 21, and the stage may be a stage that does not move in a predetermined direction.

More specifically, the microscope apparatus 20 has, for example, functions such as a Differential Interference Contrast microscope (DIC), a phase difference microscope, a fluorescence microscope, a confocal microscope, a super-resolution microscope, a two-photon excitation fluorescence microscope, a light sheet microscope, and a light field microscope.

The microscope apparatus 20 image captures a culture vessel placed on the electromotive stage 21. The culture vessel is, for example, a well plate WP, a slide chamber, or the like. The microscope apparatus 20 irradiates cell(s) cultured in a plurality of wells W provided in the well plate WP with light and thus performs image capture of transmitted light that the cell(s) have transmitted, as an image of the cell(s). In this way, the microscope apparatus 20 can acquire an image of the cell(s) such as a transmission DIC image, a phase contrast image, a dark field image, and a bright field image.

Further, the cell(s) is irradiated with excitation light exciting a fluorescent material, and thus the microscope apparatus 20 performs image capture of fluorescence emitted from a biological material, as an image of the cell(s).

In the embodiment, cell(s) are stained alive, and time-lapse image captured to acquire an image of a change of the cell(s) is obtained after cell stimulation. In the embodiment, a fluorescent fusion protein is expressed, or cell(s) is stained alive with a chemical reagent or the like to acquire a cell image. In yet another embodiment, cell(s) is fixed and stained to acquire a cell image. The fixed cell(s) stops metabolism. Accordingly, in a case where cell(s) is stimulated and subsequently a time-dependent intracellular change is observed with fixed cell(s), a plurality of cell culture vessels seeded with cell(s) are required to be prepared. For example, there is a case in which cell(s) is stimulated, and it is desired to observe a change in the cell(s) after a lapse of a first duration of time and a change in the cell(s) after a lapse of a second duration of time being different from the first duration of time. In this case, cell(s) is stimulated, and after a lapse of the first duration of time, the cell(s) is fixed and stained to acquire a cell image.

On the other hand, a cell culture vessel seeded with cell(s) different from the cell(s) used for the observation in the first duration of time is prepared. The cell(s) is stimulated and after a lapse of the second duration of time, the cell(s) is fixed and stained to acquire a cell image. In this way, a change in a cell during the first duration of time and a change in a cell during the second duration of time are observed, and thus a time-dependent intracellular change can be estimated. In addition, the number of cells used to observe the intracellular changes during the first duration of time and the second duration of time is not limited to one. Accordingly, a plurality of cell images are to be acquired during each of the first duration of time and the second duration of time. For example, in a case where the number of cells used to observe an intracellular change is 1000, 2000 cells are to be image captured during the first and second durations of time. Accordingly, in the case of attempting to acquire details of an intracellular change due to a stimulus, a plurality of cell images are required for each of timings of image capturing from when the stimulus is applied, and thus a large amount of cell images are acquired.

In addition, the microscope apparatus 20 may image capture, as the above-described cell images, luminescence or fluorescence emitted from a chromogenic material itself incorporated in a biological material; or luminescence or fluorescence emitted from a material having a chromophore and combined with a biological material. In this way, the microscope observation system 1 can acquire a fluorescence image, a confocal image, a super-resolution image, and a two-photon excitation fluorescence microscopy image.

Note that a method for acquiring an image of cell(s) is not limited to using an optical microscope. For example, the method for acquiring an image of cell(s) may be using an electron microscopy. In addition, as for the image of cell(s), a correlation may be acquired by using an image acquired by a different scheme. That is, a type of an image of cell(s) may be selected appropriately.

The cell(s) in the embodiment are, for example, primary cultured cell(s), established cultured cell(s), and cell(s) in a tissue section. To observe the cell(s), samples to be observed may be aggregations of cell(s) or tissue samples, organs, or individuals (for example, animals), and an image including cell(s) may be acquired. Note that a state of cell(s) is not particularly limited to a specific state, and the cell(s) may be in a living state or may be in a fixed state. The state of cell(s) may be "in-vitro". It goes without saying that information about the living state may be combined with information about the fixed state.

In addition, cell(s) may be treated with chemiluminescent or fluorescent proteins (for example, chemiluminescent or fluorescent proteins expressed from introduced genes (such as green fluorescent proteins (GFP))) to be observed. Alternatively, cell(s) may be observed by using staining such as immunostaining or staining with chemical reagents. The observation may be conducted by using a combination of the above-described treatment and staining. For example, a luminescent protein to be used can be selected in accordance with a determination type of an intranuclear structure (for example, Golgi body or the like) in a cell.

In addition, the pretreatment for analyzing correlation acquisition such as a means for observing cell(s), and a method for staining cell(s) may be selected appropriately in accordance with the purpose. For example, dynamic information about cell(s) may be acquired by a technique optimal for the case of acquiring a dynamic behavior of cell(s), and information about intracellular signaling pathway may be acquired by a technique optimal for the case of acquiring intracellular signaling pathway. The pretreatment selected in accordance with the purpose may be different.

The well plate WP includes one or more wells W. In the embodiment, the well plate WP includes 96 of the 8×12 wells W as illustrated in FIG. 1. The number of the well plates WP is not limited to the above and may have 48 of the 6×8 wells W. Cell(s) is cultured in the wells W under specific experimental conditions. The specific experimental conditions include temperature, humidity, a culturing period, an elapsed time period from when a stimulus is applied, a type and strength of an applied stimulus, concentration, an amount, presence or non-presence of a stimulus, induction of biological characteristics, and the like. The stimulus is, for example, a physical stimulus such as electricity, sound waves, magnetism, and light; or a chemical stimulus acquired by administering a substance or a medication. In addition, the biological characteristics are characteristics indicating a stage of cell differentiation, morphology, the number of cells, an intracellular behavior of molecules, morphology and a behavior of organelles, each of the forms, a behavior of an intranuclear structure, a behavior of DNA molecules, and the like.

Regarding Autophagy

Autophagy is an intracellular degradation system possessed by cell(s). In other words, autophagy is a phenomenon in which intracellular elements, pathogenic bacteria invading cell(s), or the like degrade. In the following description, an intracellular element, pathogenic bacteria invading cell(s), and the like are also referred to as a molecule. Specifically, autophagy is a phenomenon in which an isolation membrane is formed in a cell and in which both ends of the isolation membrane are fused together to form an autophagosome, and an intracellular element in the autophagosome degrades via a fusion process of the autophagosome with a lysosome. The lysosome contains hydrolytic enzymes. Intracellular elements isolated in the autophagosome, pathogenic bacteria, or the like degrade by fusion of the autophagosome with the lysosome.

A formation process of the autophagosome will be described here. The isolation membrane extends, and both ends of the isolation membrane are fused together to isolate the degrading intracellular elements. The state where the isolation membrane isolates the intracellular elements is a state where the autophagosome is formed. The isolated intracellular element degrades by fusion of the autophagosomes with the lysosomes. The degradation of the intracellular elements by autophagy in a cell is also referred to as autophagic activity. Autophagy has a plurality of types. In the embodiment, two types of a non-selective autophagy and a selective autophagy will be described by way of example.

Figure 2:
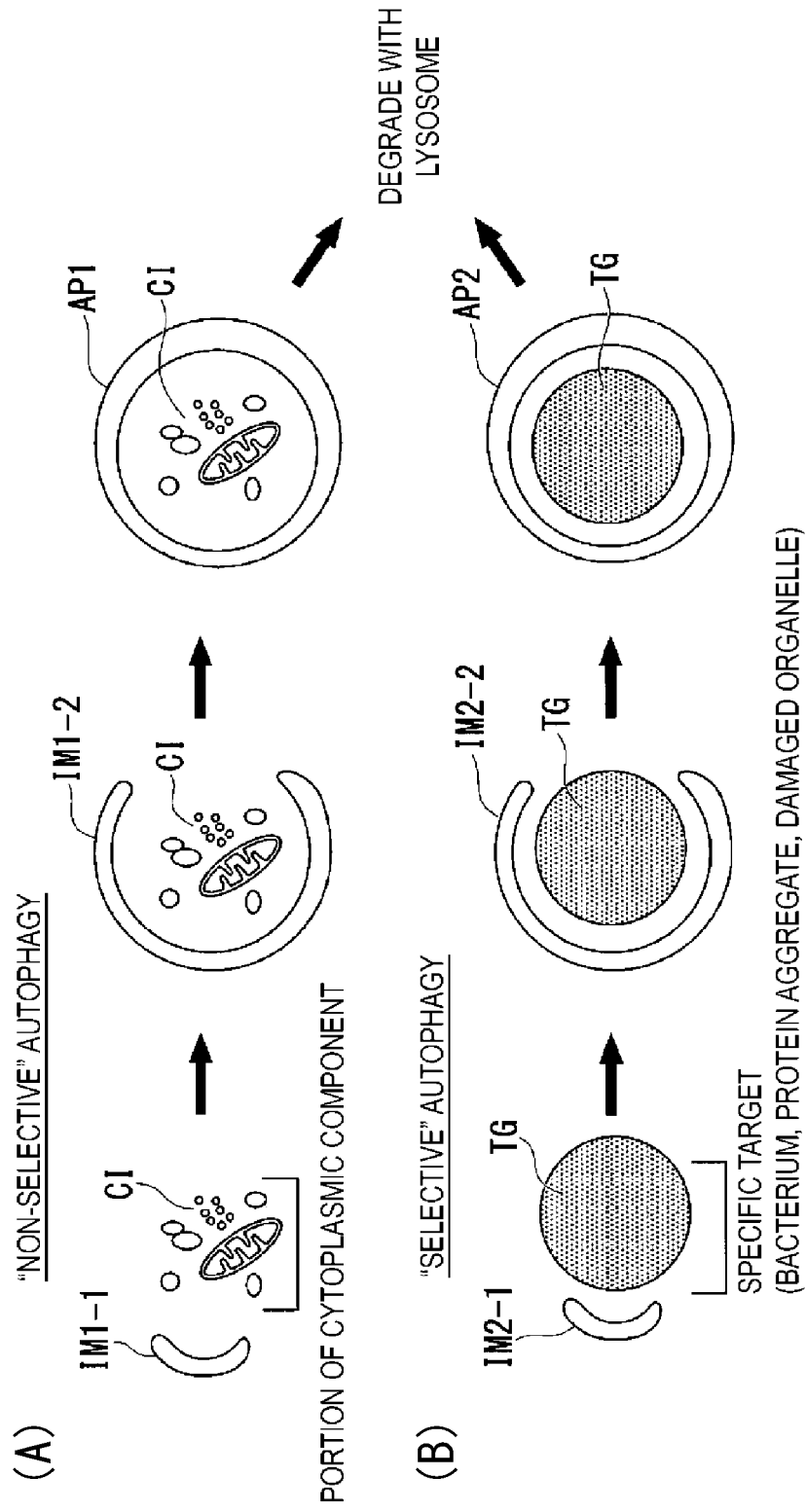
FIG. 2 is a view illustrating an example of a non-selective autophagy and a selective autophagy.

With reference to FIG. 2, the non-selective autophagy and the selective autophagy will be described here.

FIG. 2 is a view illustrating an example of the non-selective autophagy and the selective autophagy.

Part (A) of FIG. 2 is a view illustrating an example of the formation of the non-selective autophagy. As illustrated in part (A) of FIG. 2, the non-selective autophagy forms an isolation membrane IM1-1 and incorporates an intracellular element CI. The isolation membrane IM1-1 extends as illustrated by an isolation membrane IM1-2 to form an autophagosome AP1 having incorporated the intracellular element CI. The autophagosome AP1 fuses with a lysosome and degrades the intracellular element CI.

Part (B) of FIG. 2 is a view illustrating an example of the formation of the selective autophagy. As illustrated in part (B) of FIG. 2, the selective autophagy forms an isolation membrane IM2-1 and incorporates a specific target TG. The specific target TG is a bacterium, a protein aggregate including agglomerated abnormal proteins, or an organelle being a damaged cell organelle. The selective autophagy degrades the specific target TG alone. For example, in a case where a bacterium is the specific target TG, the selective autophagy degrades the bacterium at a location where an intracellular bacterium exists. Accordingly, at a location where no intracellular bacterium exists, no degradation by the selective autophagy occurs. The isolation membrane IM2-1 extends as illustrated by an isolation membrane IM2-2 to form an autophagosome AP2 having incorporated the specific target TG. The autophagosome AP2 fuses with the lysosome and degrades the specific target TG. The specific target TG that the selective autophagy degrades at one time is a molecule smaller in size than the intracellular element CI that the non-selective autophagy degrades at one time. In addition, the number of molecules that the selective autophagy degrades at one time is less than the number of molecules that the non-selective autophagy degrades at one time.

The autophagic activity described above is observed by fluorescent staining of a marker protein LC3 (Microtubule-associated protein light chain 3) and a marker protein Atg5 (Autophagy-related gene 5) and then observing fluorescence.

Next, molecular congestion in cell(s) that varies owing to degradation of intracellular elements due to autophagy will be described. The molecular congestion refers to a state where cell(s) is filled with various types of proteins or the like. Accordingly, the cell(s) contain molecules. In addition, the cell(s) contains subcellular components including molecules. The cell(s) contains polymers having a high molecular weight such as proteins. The molecular congestion refers to a degree of clogging of molecules that the cell(s) contain. The molecular congestion indicates a degree of congestion of molecules in the cell(s). The degree of congestion of molecules in the cell(s) can also be referred to as intracellular molecular density. The molecular congestion indicates a degree of intracellular molecular expansion. The intracellular molecular density refers to volume of molecules present in a prescribed volume. When autophagic activity is suppressed, the molecular congestion in the cell(s) increases. When autophagic activity is promoted, the molecular congestion in the cell(s) decreases. Variation in the molecular congestion will be described below.

In the embodiment, the cell(s) is fluorescent stained with GimRET (Glycine inserted mutant fRET sensor), and the state of molecular congestion is observed. For example, GimRET is described in Takamitsu J. Morikawa, Hideaki Fujita, Akira Kitamura, Takashi Horio, Johtaro Yamamoto, Masataka Kinjo, Akira Sasaki, Hiroaki Machiyama, Keiko Yoshizawa, Taro Ichimura, Katsumi Imada, Takeharu Nagai & Tomonobu M. Watanabe, Scientific Reports 6, Article number: 22342 (2016). The cell(s) fluorescent stained with GimRET change a luminescent color in accordance with a state of molecular congestion in cell(s). The image processing device 10 determines the change in the state of molecular congestion in the cell(s) by observing the change in the color of the cell(s) stained with GimRET. Note that the state of molecular congestion may be observed by another method without being limited to the method of fluorescent staining with GimRET.

The image processing device 10 determines the type of an intracellular autophagy on the basis of the degree of autophagic activity and the state of molecular congestion. In the embodiment, the image processing device 10 determines whether the autophagy induced in the cell(s) is the selective autophagy or the non-selective autophagy.

Functional Configuration of Image Processing Device

Next, with reference to FIG. 3, an example of a functional configuration of the image processing device 10 will be described.

Figure 3:
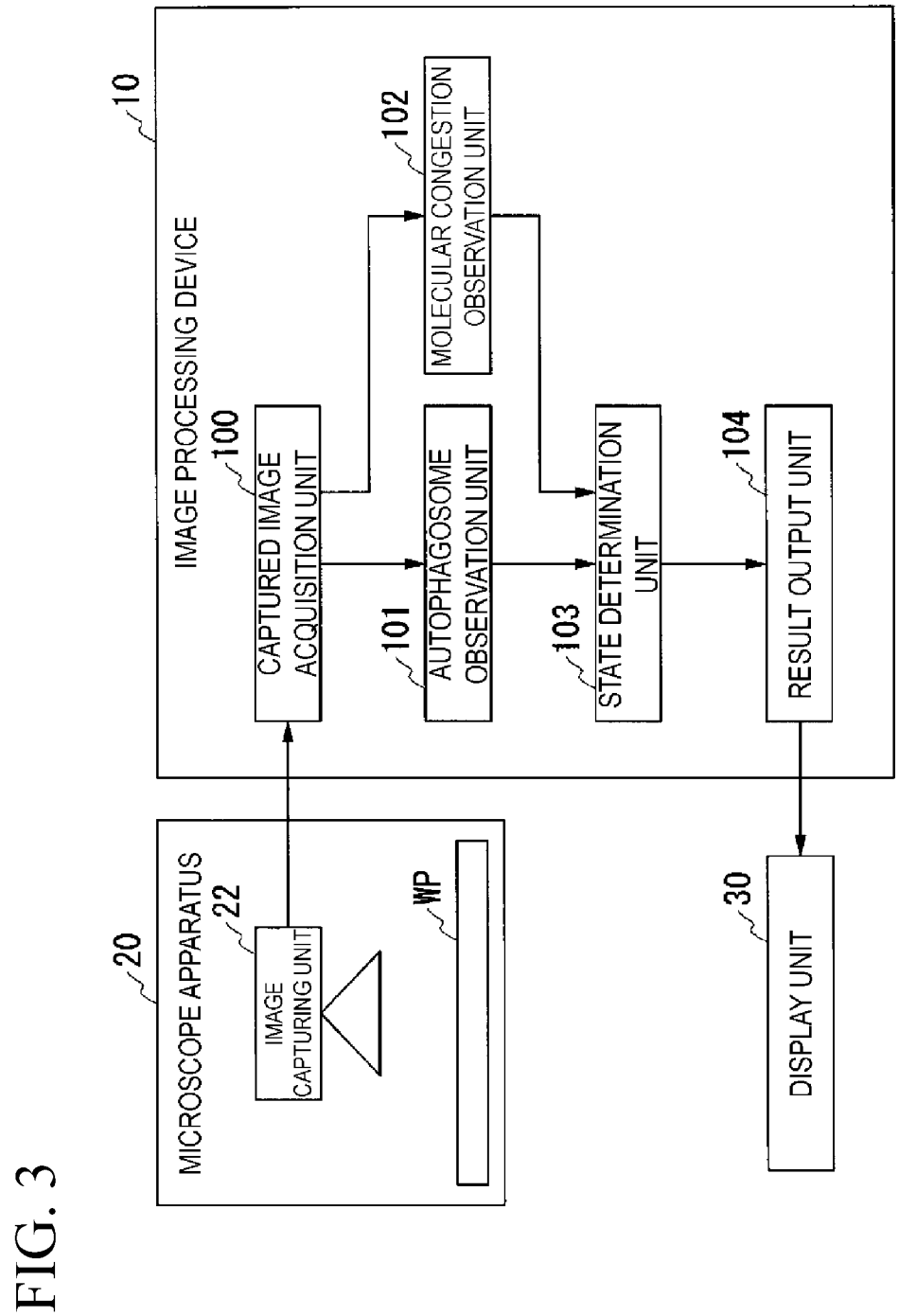
FIG. 3 is a view illustrating an example of a functional configuration of each of units provided in an image processing device according to an embodiment.

FIG. 3 is a view illustrating a functional configuration of each of units provided in the image processing device 10 according to the embodiment. The image processing device 10 is a computer device configured to analyze an image captured by the microscope apparatus 20.

The image processing device 10 includes a captured image acquisition unit 100, an autophagosome observation unit 101, a molecular congestion observation unit 102, a state determination unit 103, and a result output unit 104.

Note that an image to be processed by the image processing device 10 is not limited to the image captured by the microscope apparatus 20 and may be an image stored in advance in a storage unit (not illustrated) provided in the image processing device 10 or may be an image stored in advance in an external storage device (not illustrated), for example.

The image processing device 10 functions by a program stored in the storage unit (not illustrated) and executed by a processor. In addition, some or all of these functional units of the image processing device 10 may include a hardware such as a Large Scale Integration (LSI) or an Application Specific Integrated Circuit (ASIC).

The captured image acquisition unit 100 acquires a cell image captured by the image capturing unit 22 and feeds the acquired cell image to the autophagosome observation unit 101 and the molecular congestion observation unit 102. Here, the cell image to be acquired by the captured image acquisition unit 100 include a plurality of images in which cell culture states are image captured in time series; and a plurality of images in which cell(s) cultured under various experimental conditions are image captured.

The image capturing unit 22 image captures at a time interval required for the formation of an autophagosome in cell(s) cultured in the well plate WP. The formation of an autophagosome requires, for example, a time of approximately 10 minutes until when the isolation membrane is formed to complete the formation of an autophagosome. The image capturing unit 22 image captures the well plate WP at an interval of approximately 10 minutes to image capture the intracellular formation process of an autophagosome. Note that the interval at which the image capturing unit 22 image captures is not limited to the above-described time interval. The image capturing unit 22 may image capture the intracellular formation process of an autophagosome at a time interval of less than 10 minutes; or at a time interval of approximately 30 minutes.

In addition, the image capturing unit 22 image captures the intracellular formation process of an autophagosome for two hours or more after the starting of image capturing the well plate WP at the time interval described above. This is because autophagy requires not less than two hours to affect a total protein amount of the whole cell(s). Note that the time for image capturing may be two hours or less.

In addition, in the case of observing a growth rate of the cell(s), the image capturing unit 22 image captures the well plate WP at a time interval of 24 hours or more after the starting of image capturing the well plate WP. This is because a time-lapse of approximately 24 hours is required for the change in the number of cells. Note that the time for image capturing may be 24 hours or less.

The autophagosome observation unit 101 acquires a cell image from the captured image acquisition unit 100. The autophagosome observation unit 101 observes the number of autophagosomes present in the cell image acquired from the captured image acquisition unit 100. Specifically, the autophagosome observation unit 101 counts the fluorescence number emitted from the marker protein LC3 fluorescent stained in the cell(s) and the marker protein Atg5 fluorescent stained in the cell(s).

The autophagosome observation unit 101 feeds the counted number of the autophagosomes to the state determination unit 103.

The molecular congestion observation unit 102 acquires a cell image from the captured image acquisition unit 100. The molecular congestion observation unit 102 observes the state of the molecular congestion of the image captured cell(s) from the cell image acquired from the captured image acquisition unit 100. The molecular congestion observation unit 102 feeds the observed state of molecular congestion to the state determination unit 103.

The state determination unit 103 acquires the number of autophagosomes from the autophagosome observation unit 101. The state determination unit 103 acquires the state of molecular congestion from the molecular congestion observation unit 102. The state determination unit 103 determines the type of autophagy on the basis of the number of autophagosomes and the state of molecular congestion. In other words, the state determination unit 103 determines whether the autophagy is a selective autophagy or a non-selective autophagy on the basis of the time-lapse change in the number of autophagosomes and the time-lapse change in the state of molecular congestion. A criterion for the state determination unit 103 to determine whether the autophagy is a selective autophagy or a non-selective autophagy will be described below.

The state determination unit 103 feeds the determination result to the result output unit 104.

The result output unit 104 acquires the determination result of whether an active autophagy is a selective autophagy or a non-selective autophagy from the state determination unit 103. The result output unit 104 causes the display unit 30 to display the acquired determination result. The display unit 30 displays the determination result.

Example of Processing of Image Processing Device

Next, with reference to FIG. 4, an example of processing in which the image processing device 10 determines the type of autophagy will be described.

Figure 4:
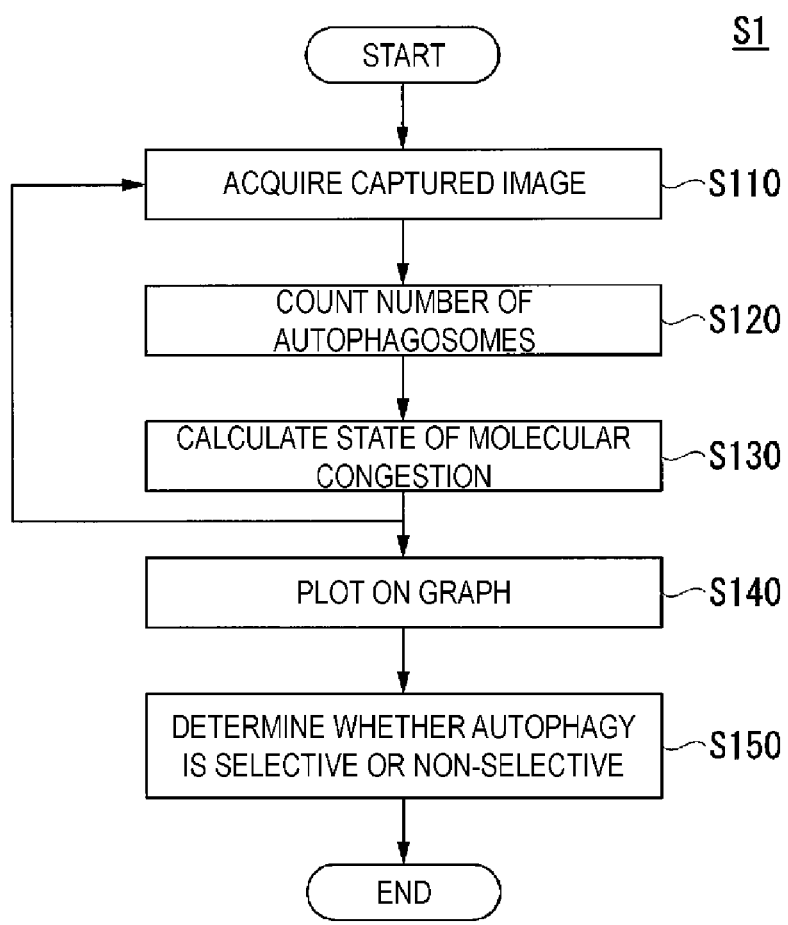
FIG. 4 is a flowchart illustrating an example of processing in which an image processing device determines a type of autophagy.

FIG. 4 is a flowchart illustrating an example of processing in which the image processing device 10 determines the type of autophagy. Note that the processing procedure described here is an example, and a processing procedure may be omitted, or another processing procedure may be added.

The captured image acquisition unit 100 acquires a cell image from the microscope apparatus 20 (step S110). The captured image acquisition unit 100 feeds the cell image acquired from the microscope apparatus 20 to the autophagosome observation unit 101. The autophagosome observation unit 101 acquires the cell image from the captured image acquisition unit 100. The autophagosome observation unit 101 counts the number of autophagosomes image captured in the cell image acquired from the captured image acquisition unit 100 (step S120). The autophagosome observation unit 101 feeds the counted number of the autophagosomes to the state determination unit 103.

The captured image acquisition unit 100 feeds the cell image acquired from the microscope apparatus 20 to the molecular congestion observation unit 102. The molecular congestion observation unit 102 acquires the cell image from the captured image acquisition unit 100. The molecular congestion observation unit 102 calculates a state of the molecular congestion of the cell(s) image captured in the cell image acquired from the captured image acquisition unit 100 (step S130). The molecular congestion observation unit 102 feeds the calculated state of molecular congestion to the state determination unit 103.

The state determination unit 103 acquires the number of autophagosomes from the autophagosome observation unit 101. The state determination unit 103 acquires the state of molecular congestion from the molecular congestion observation unit 102. The image processing device 10 repeats the processing from step S110 to step S130 until the number of autophagosomes and the state of molecular congestion for a predetermined amount of time are acquired. Note that the image processing device 10 may acquire a cell image in a state in which the cell image is associated with the time when the cell image is captured and may calculate at one time the number of autophagosomes and the state of molecular congestion for each time when the cell image is captured. In addition, the processing at step S120 may be performed before or after the processing at step S130.

Figure 5A:
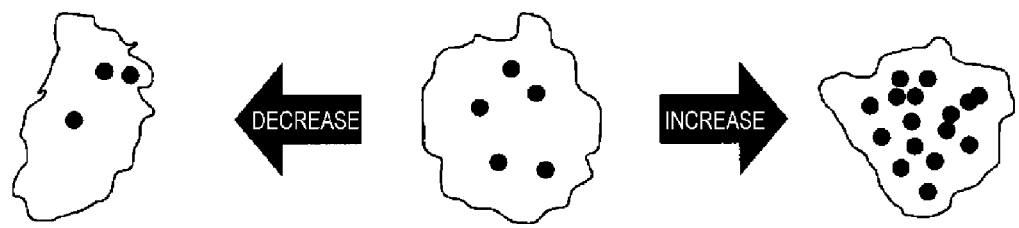
FIGS. 5A and 5B illustrate an example of a change in the number of autophagosomes in cell(s) and a change in a state of molecular congestion.
Figure 5B:
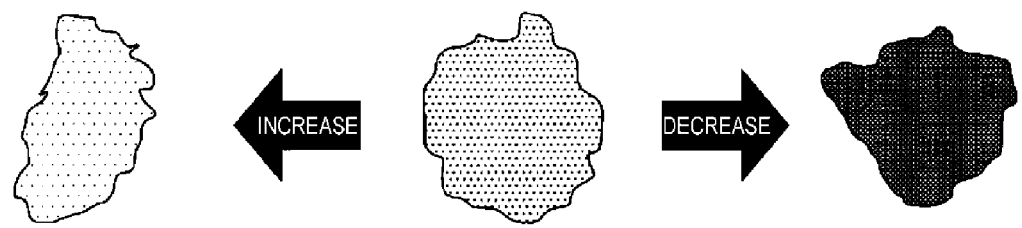

With reference to FIGS. 5A and 5B, an example of the number of autophagosomes observed by the autophagosome observation unit 101 and an example of the state of molecular congestion observed by the molecular congestion observation unit 102 will be described here.

FIGS. 5A and 5B are views illustrating an example of a change in the number of autophagosomes in cell(s) and a change in the state of molecular congestion.

FIG. 5A illustrates an increase and a decrease in the number of autophagosomes. The autophagosome observation unit 101 counts the number of autophagosomes. Specifically, the autophagosome observation unit 101 observes fluorescence from a marker protein LC3 and fluorescence from a marker protein Atg5 and counts the number of autophagosomes. In an example illustrated in FIG. 5A, the case where the number of autophagosomes decreases from 5 to 2 and the case where the number of autophagosomes increases from 5 to 16 are illustrated.

FIG. 5B is a view illustrating a change in the state of molecular congestion. In this example, the molecular congestion observation unit 102 observes the state of molecular congestion in accordance with a change in colors of the image captured fluorescence. When the molecular congestion changes, the colors of the fluorescence change. The molecular congestion observation unit 102 determines an increase and a decrease in the molecular congestion in accordance with the colors of the fluorescence.

With reference to FIG. 4 again, the state determination unit 103 plots the acquired number of autophagosomes and the acquired state of molecular congestion in a time series (step S140).

The state determination unit 103 determines the type of autophagy generated in the cell(s) on the basis of the acquired number of autophagosomes and the acquired state of molecular congestion. In the embodiment, the state determination unit 103 determines, on the basis of the number of autophagosomes and the change in the state of molecular congestion, whether the number of generated selective autophagy is greater or the number of generated non-selective autophagy is greater, among the intracellular autophagy (step S150).

Figure 6:
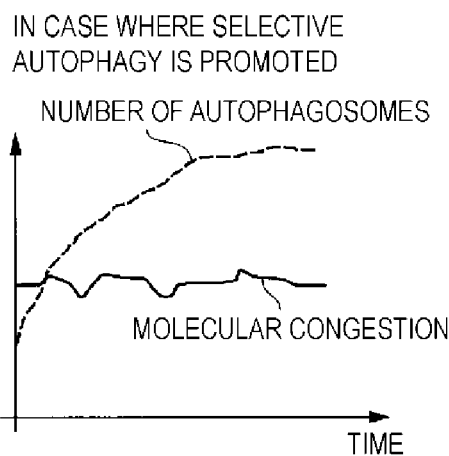
FIG. 6 is a view illustrating an example of a graph on which the number of autophagosomes and a state of molecular congestion are plotted.
Figure 6:
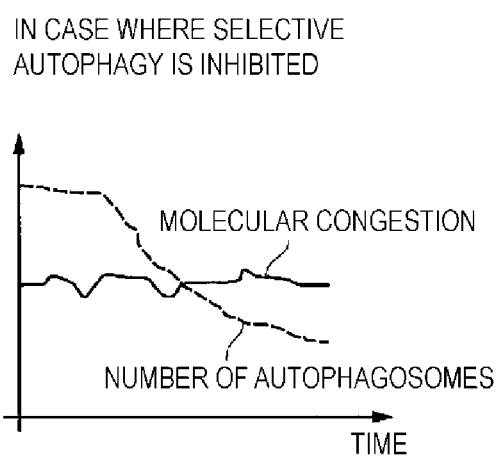
Figure 6:
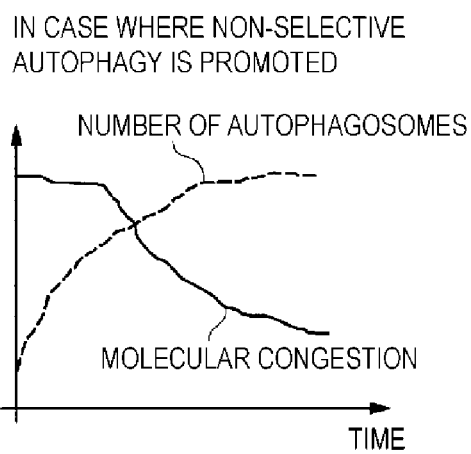
Figure 6:
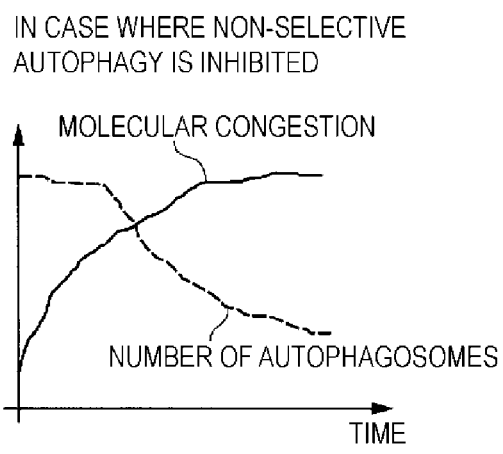

With reference to FIG. 6, a criterion for the state determination unit 103 to determine whether autophagic activity is a selective autophagy or a non-selective autophagy will be described here.

FIG. 6 is a view illustrating an example of a graph on which the number of autophagosomes and the state of molecular congestion are plotted.

FIG. 6A-1 is a view illustrating an example of a graph in a case where the selective autophagy has been promoted in cell(s). In a case where the number of the generated selective autophagy is greater, the number of autophagosomes increases over time, and there is no significant increase nor decrease in the molecular congestion. In this case, the state determination unit 103 determines that the selective autophagy has been promoted in the cell(s).

FIG. 6A-2 is a view illustrating an example of a graph in a case where the selective autophagy has been inhibited in cell(s). In a case where the selective autophagy is inhibited, the number of autophagosomes decreases over time, and there is no significant increase nor decrease in the molecular congestion. In this case, the state determination unit 103 determines that the selective autophagy has been inhibited in the cell(s).

That is, the molecular congestion is difficult to change due to the selective autophagy. This is because the selective autophagy selects specific molecules, that is, the selective autophagy only degrades a portion and a fraction of the intracellular elements, thus the selective autophagy has less influence on the number of intracellular molecules as compared to the non-selective autophagy, and the molecular congestion is difficult to increase and decrease.

FIG. 6B-1 is a view illustrating an example of a graph in a case where the non-selective autophagy has been promoted in cell(s). In a case where the non-selective autophagy is promoted, the number of autophagosomes increases over time, and the molecular congestion decreases. In this case, the state determination unit 103 determines that the selective autophagy has been promoted in the cell(s).

The non-selective autophagy is promoted, and thus, the molecular congestion decreases. This is because the non-selective autophagy degrades a plurality of molecules at any location in the cell at one time, and thus the number of intracellular molecules decreases.

FIG. 6B-2 is a view illustrating an example of a graph in a case where the non-selective autophagy has been inhibited in cell(s). In a case where the non-selective autophagy is inhibited, the number of autophagosomes decreases over time, and the molecular congestion increases. In this case, the state determination unit 103 determines that the selective autophagy has been inhibited in the cell(s).

Overview of First Embodiment

There has been a demand for a method for determining whether autophagy degrading intracellular elements is a non-selective autophagy degrading a portion of the intracellular elements or a selective autophagy degrading specific intracellular elements. The image processing device 10 includes the autophagosome observation unit 101, the molecular congestion observation unit 102, and the state determination unit 103. The autophagosome observation unit counts the number of autophagosomes in cell(s). The molecular congestion observation unit 102 observes the state of molecular congestion in cell(s). The state determination unit 103 determines whether an activated autophagy is a selective autophagy or a non-selective autophagy, on the basis of the time-lapse change in the number of autophagosomes in cell(s) and the time-lapse change in the state of molecular congestion. In this way, the image processing device 10 can determine the state of the intracellular autophagy. In other words, the image processing device 10 can determine whether autophagy degrading the intracellular elements is a non-selective autophagy degrading a portion of intracellular elements or a selective autophagy degrading specific intracellular elements.

In addition, the state determination unit 103 described above may determine the state of autophagic activity by performing a comparison of information as a criterion indicative of the number of autophagosomes and the state of molecular congestion with the number of autophagosomes and the state of molecular congestion acquired from the cell image. In this case, the information as the criterion may be stored in a storage unit (not illustrated) in advance.

Note that in the embodiment described above, the autophagosome observation unit 101 counts the number of autophagosomes image captured in the cell image and feeds the counted number of autophagosomes to the state determination unit 103, but the information to be supplied is not limited to the counted number of autophagosomes. The autophagosome observation unit 101 may detect an increase and a decrease in the number of autophagosomes alone and may provide information about the activation state of whether the autophagosome is active or non-active to the state determination unit 103. In addition, the autophagosome observation unit 101 may detect whether an autophagosome has occurred and may supply the detection information to the state determination unit 103 as information about the activation state of the autophagosome.

In addition, in the embodiment described above, the state determination unit 103 determines whether the activated autophagy is a selective autophagy or a non-selective autophagy on the basis of, but not limited to, the time-lapse change in the number of autophagosomes and the time-lapse change in the state of molecular congestion.

In place of the time-lapse change in the number of autophagosomes, at least one of the information about an increase and a decrease in the number of autophagosomes or the information about whether the autophagosome has occurred may be used. For example, the state determination unit 103 may determine whether autophagy is a selective autophagy or a non-selective autophagy on the basis of an increase and a decrease of the autophagy and the state of molecular congestion. In addition, for example, the state determination unit 103 may determine whether autophagy is a selective autophagy or a non-selective autophagy on the basis of the information about whether the autophagosome has occurred and the state of molecular congestion. In this case, the time for acquiring the information about an increase and a decrease of the autophagy or the information about whether the autophagosome has occurred can be reduced, as compared to the time-lapse change in the number of autophagosomes.

In addition, in the embodiment described above, although the state determination unit 103 determines whether the activated autophagy is a selective autophagy or a non-selective autophagy on the basis of the time-lapse change in the number of autophagosomes and the time-lapse change in the state of molecular congestion, the state determination unit 103 may determine whether the activated autophagy is a selective autophagy or a non-selective autophagy, based on the time-lapse change in the state of molecular congestion alone. Since there is a case where the state of cell(s) changes over time irrespective of the autophagy, for example, due to cell division and the molecular congestion changes over time, the information about the time-lapse change in the number of autophagosomes is used, in addition to the time-lapse change in the state of molecular congestion, to determine whether the activated autophagy is a selective autophagy or a non-selective autophagy. However, in a case where the relationship between the time-lapse change in the state of molecular congestion and the information about the time-lapse change in the number of autophagy is apparent in advance, the autophagosome observation unit 101 may determine whether the activated autophagy is a selective autophagy or a non-selective autophagy, on the basis of the information about the time-lapse change in the state of molecular congestion without counting the number of autophagosomes image captured in the cell image.

In addition, in the embodiment described above, the configuration in which the image processing device 10 includes the captured image acquisition unit 100 is described; however, the image processing device 10 may not include the microscope apparatus 20 and/or the captured image acquisition unit 100. In this case, the image processing device 10 may determine the type of autophagy induced in cell(s) on the basis of the cell images stored in advance in the storage unit (not illustrated).

Since the captured image acquisition unit 100 can acquire a cell image captured by the microscope apparatus 20, time and labor can be saved, as compared to the case where the cell image is acquired via another device.

In addition, in the embodiment described above, the information about the time-lapse change in the state of molecular congestion is used; however, the information about the change in the molecular congestion may be used alone, except for the information about the time-lapse change in the molecular state. For example, the state of the molecular congestion of the cell(s) before application of a stimulus may be stored as information being a criterion in a storage unit (not illustrated), and a result of a comparison of the molecular state during predetermined time with the information being the criterion may be used as the information about the state of molecular congestion.

Note that in the embodiment described above, the state determination unit specifies the types of the selective autophagy and the non-selective autophagy among the types of the autophagy generated in the cell(s), on the basis of the acquired number of autophagosomes and the state of molecular congestion; however, the types of the selective autophagy and the non-selective autophagy may not be specified as such. For example, there is a case where there are two types of selective autophagy induced in the cell(s) in the selective autophagy. In this case, an amount of degradation of one of the selective autophagy may be greater than an amount of degradation of the non-selective autophagy. In this case, the state determination unit may determine, on the basis of the acquired number of autophagosomes and the state of molecular congestion, whether a type of autophagy generated in the cell(s) is the type of autophagy that changes the state of molecular congestion, or the type of autophagy that does not change the state of molecular congestion. That is, the type of autophagy may be determined not only as the selective autophagy or the non-selective autophagy, but also as a type of autophagy that changes the state of molecular congestion or a type of autophagy that does not change the state of molecular congestion. In addition, for example, the type of autophagy that changes the state of molecular congestion may be a change amount in the state of molecular congestion for predetermined time. For example, in a case where two different types of autophagy are to be determined, the two different types of autophagy may be determined based on a difference in the change amount for predetermined time. For example, in a case where the molecular congestion of the two types of autophagy decreases, the two types of autophagy may be determined based on a difference in the decrease amount of the molecular congestion for predetermined time.

Second Embodiment

The case where the image processing device determines whether the intracellular autophagy is a selective autophagy or a non-selective autophagy is described above. Next, with reference to FIG. 7, a case where an image processing device determines whether a stimulus from a medication or the like induces a selective autophagy or a non-selective autophagy and determines an influence of the stimulus on a change in the number of cells. Note that the same configurations and operations as those in the first embodiment are denoted by the same reference signs, and the description of the same configurations and operations will be omitted.

Figure 7:
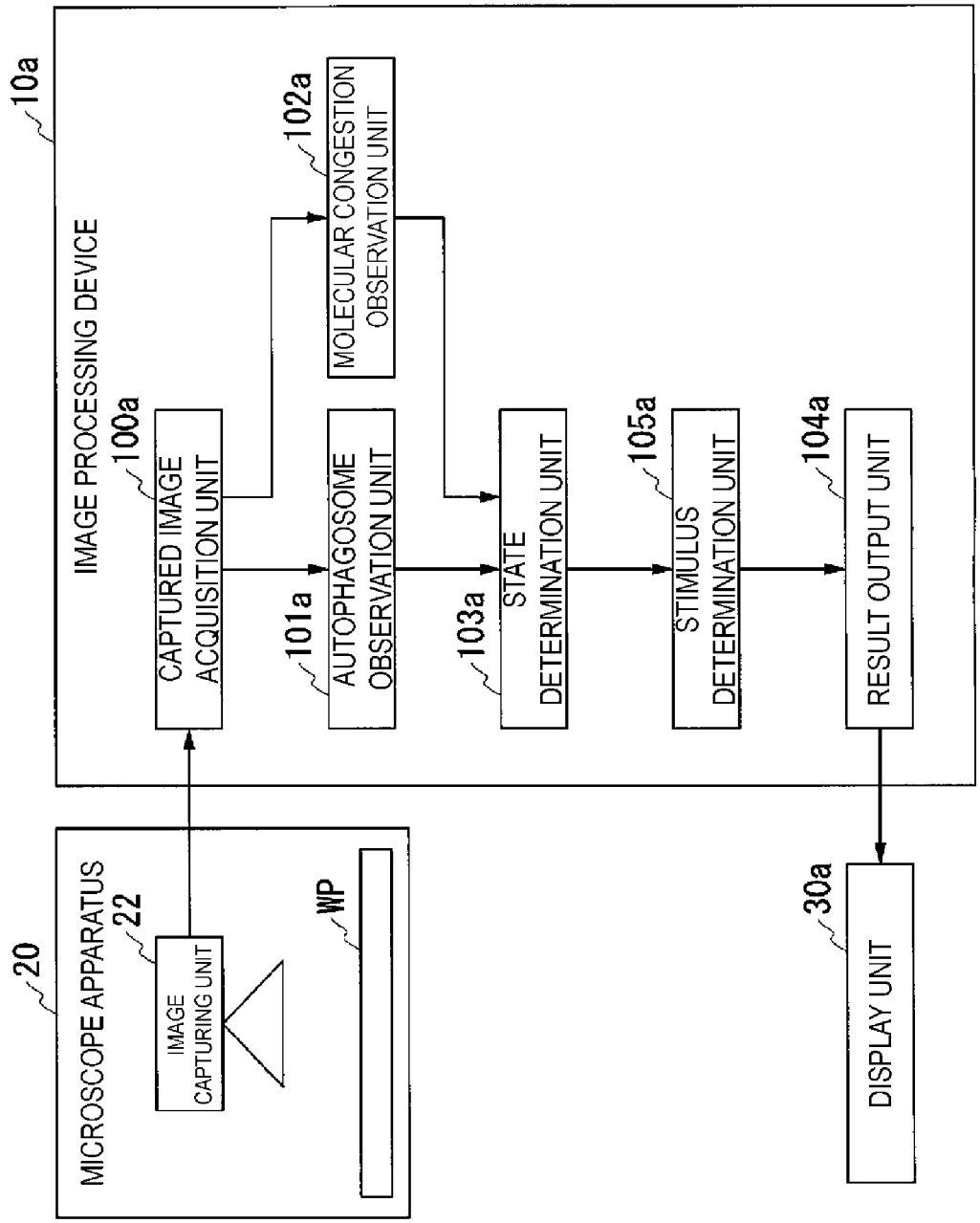
FIG. 7 is a view illustrating an example of a functional configuration of an image processing device.

FIG. 7 is a view illustrating an example of a functional configuration of an image processing device 10a.

The image processing device 10a includes a captured image acquisition unit 100a, an autophagosome observation unit 101a, a molecular congestion observation unit 102a, a state determination unit 103a, a stimulus determination unit 105a, and a result output unit 104a.

The captured image acquisition unit 100a acquires a plurality of cell images captured by the image capturing unit 22 and experimental conditions in association with each other. The experimental conditions are information about a medication or the like administered to cell(s) image captured in the cell images. The cell images captured by the captured image acquisition unit 100a include images in which stimulated cell(s) is image captured and images in which cell(s) cultured without stimulus are image captured. The cell(s) cultured without stimulus is cell(s) cultured under the same conditions as the conditions for the stimulated cell(s), excluding the condition of presence or non-presence of a stimulus. In the following description, the cell(s) cultured without stimulus is also referred to as control cell(s). In these cases, a storage unit (not illustrated) may include an experimental condition storage unit. The experimental condition storage unit stores, for each of the cell images, information about the experimental conditions for the cell(s) associated with the cell image.

The captured image acquisition unit 100a feeds the cell images to the autophagosome observation unit 101a and the molecular congestion observation unit 102a.

The autophagosome observation unit 101a acquires the cell images from the captured image acquisition unit 10a. The autophagosome observation unit 101a counts the number of autophagosomes for each of the cell images. In addition, the autophagosome observation unit 101a also counts the number of the cells for each of the cell images. The autophagosome observation unit 101a feeds the counted number of autophagosomes and the number of the cells to the state determination unit 103a.

The molecular congestion observation unit 102a acquires the cell images from the captured image acquisition unit 100a. The molecular congestion observation unit 102a observes a state of the molecular congestion of the image captured cell(s) from the cell images acquired from the captured image acquisition unit 100a. The molecular congestion observation unit 102a feeds the observed state of molecular congestion to the state determination unit 103a.

The state determination unit 103a acquires the number of autophagosomes and the number of the cells from the autophagosome observation unit 101a. The state determination unit 103a acquires the state of molecular congestion from the molecular congestion observation unit 102a. The state determination unit 103a stores the number of autophagosomes and the state of molecular congestion together with the experimental conditions. The state determination unit 103a measures, for each of the experimental conditions, a time-lapse change in the number of autophagosomes, a time-lapse change in the number of the cells, and a time-lapse change in the state of molecular congestion. The state determination unit 103a plots a graph, for each of the experimental conditions, on the basis of the measured change in the number of autophagosomes, the measured change in the number of the cells, and the measured change in the state of molecular congestion.

The state determination unit 103a feeds the graph to the stimulus determination unit 105a.

The stimulus determination unit 105a acquires the graph from the state determination unit 103a. The stimulus determination unit 105a, on the basis of the graph acquired from the state determination unit 103a, determines whether a stimulus that the cell(s) has received induces a selective autophagy or a non-selective autophagy and determines an influence of the stimulus on the change in the number of the cells. Note that whether a stimulus that the cell(s) has received induces or inhibits a selective autophagy or a non-selective autophagy may be determined not only based on the graph acquired from the state determination unit 103a, but also based on mathematical analysis on numerical values.

The stimulus determination unit 105a feeds the determination result to the result output unit 104a. The result output unit 104a causes a display unit 30a to display the determination result acquired from the stimulus determination unit 105a.

Example of Processing of Image Processing Device According to Second Embodiment

Next, with reference to FIG. 8, an example of processing in which the image processing device 10a determines whether a stimulus applied to cell(s) induces a selective autophagy or a non-selective autophagy and determines an influence of the stimulus on a change in the number of the cells will be described.

Figure 8:
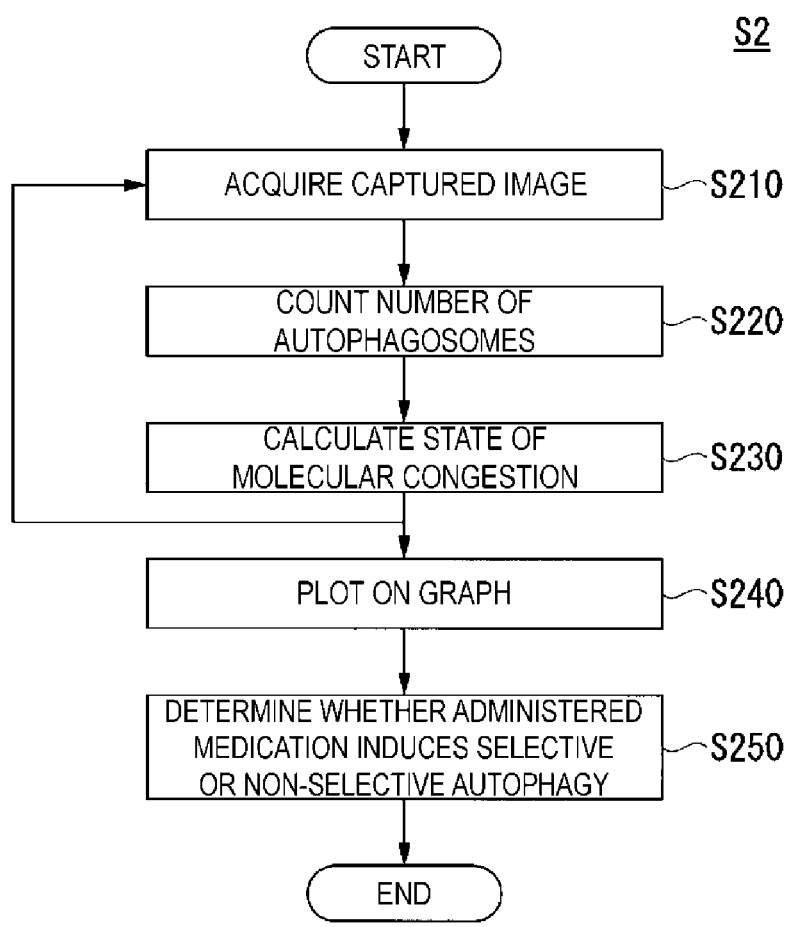
FIG. 8 is a flowchart illustrating an example of processing in which an image processing device according to a second embodiment determines a change of a state of autophagic activity of cell(s) due to a stimulus and an influence of the stimulus on a change in the number of the cell(s).

FIG. 8 is a flowchart illustrating an example of processing in which the image processing device 10a according to the second embodiment determines a change in a state of autophagic activity of the cell(s) due to a stimulus and an influence of the stimulus on a change in the number of the cells. Note that the processing procedure described here is an example, and a processing procedure may be omitted, or another processing procedure may be added.

The captured image acquisition unit 100a acquires a cell image from the microscope apparatus 20 together with experimental conditions for the cell(s) (step S210). The captured image acquisition unit 100a feeds the cell image acquired from the microscope apparatus 20 and the experimental conditions in association with each other to the autophagosome observation unit 101a. The autophagosome observation unit 101a acquires the cell image and the experimental conditions from the captured image acquisition unit 100a. The autophagosome observation unit 101a counts the number of autophagosomes image captured in the cell image acquired from the captured image acquisition unit 100a. In addition, the autophagosome observation unit 101a counts the number of the cells image captured in the cell image (step S220). The autophagosome observation unit 101a feeds the counted number of autophagosomes, the counted number of the cells, and the experimental conditions in association with one another to the state determination unit 103a.

The captured image acquisition unit 100a feeds the cell image acquired from the microscope apparatus 20 and the experimental conditions in association with each other to the molecular congestion observation unit 102a. The molecular congestion observation unit 102a acquires the cell image and the experimental conditions from the captured image acquisition unit 100a. The molecular congestion observation unit 102a calculates the state of the molecular congestion of the cell(s) image captured in the cell image acquired from the captured image acquisition unit 100a (step S230). The molecular congestion observation unit 102a feeds the calculated state of molecular congestion and the experimental conditions in association with each other to the state determination unit 103a.

The state determination unit 103a acquires the number of autophagosomes, the number of the cells, and the experimental conditions from the autophagosome observation unit 101a. The state determination unit 103a acquires the state of molecular congestion and the experimental conditions from the molecular congestion observation unit 102a. The state determination unit 103a measures, for each of the experimental conditions, a time-lapse change in the number of autophagosomes, a time-lapse change in the state of molecular congestion, and a time-lapse change in the number of the cells. The image processing device 10a repeats processing from step S210 to step S230 until the number of autophagosomes and the state of molecular congestion for a predetermined amount of time are acquired. The state determination unit 103a plots a graph, for each of the experimental conditions, on the basis of the measured time-lapse change in the number of autophagosomes and the measured time-lapse change in the number of the cells (step S240). The state determination unit 103a feeds the graph to the stimulus determination unit 105a.

Note that the image processing device 10a may acquire the cell image in a state in which the cell image is associated with the time when the cell image is captured and the experimental conditions in association with each other and may calculate, at one time, the number of autophagosomes, the number of the cells, and the state of molecular congestion for each time when the cell image is captured. In addition, the processing at step S220 may be performed before or after the processing at step S230.

Figure 9:
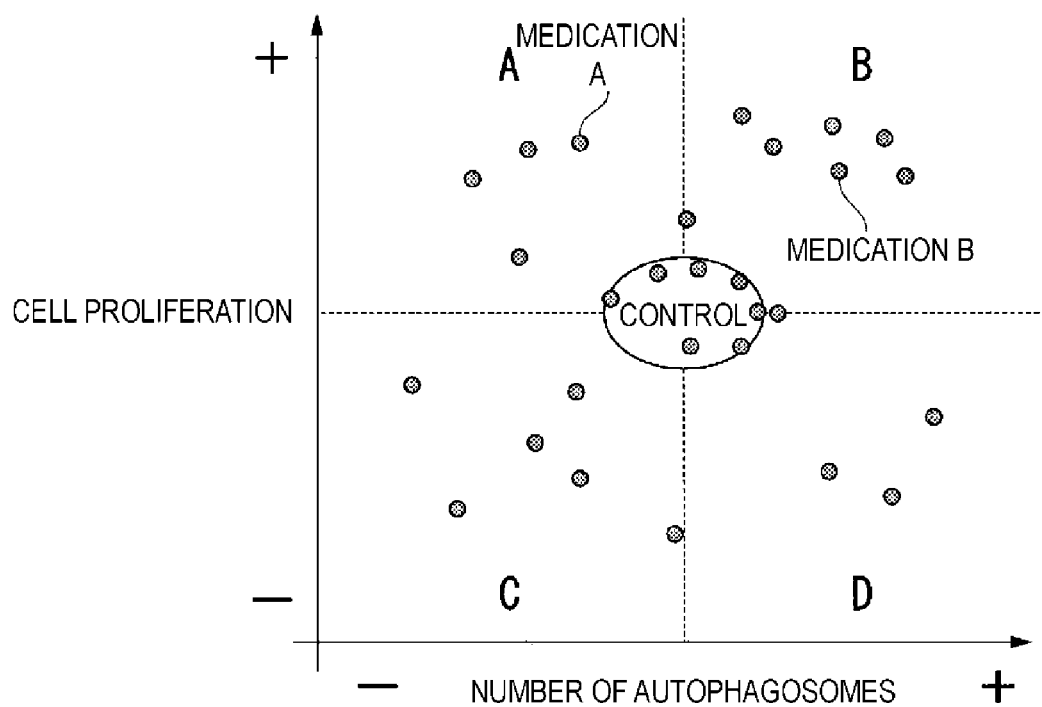
FIG. 9 is a graph having a plot of a change in the number of autophagosomes versus a change in a cell proliferation state for each of medications with types of the medications being as experimental conditions.

With reference to FIG. 9, a graph generated by the state determination unit 103a will be described here.

FIG. 9 is a graph having a plot of a change in the number of autophagosomes versus a change in a cell proliferation state for each of medications with types of the medications being as the experimental conditions. The cell proliferation state refers to a state in which the number of cells increases and decreases due to a stimulus of the medications. The graph includes a region A, a region B, a region C, and a region D.

The region A is a region where cell(s) proliferate and the number of autophagosomes decreases. The region B is a region where cell(s) proliferate and the number of autophagosomes increases. The region C is a region where cell(s) decrease and the number of autophagosomes decreases. The region D is a region where cell(s) decrease and the number of autophagosomes increases. A region indicated by CONTROL is a region having a plot on the basis of a time-lapse change in the cell number of control cell(s) used for comparison with stimulated cell(s), and a time-lapse change in the number of autophagosomes. The medications having plots at positions separated away from the region indicated by CONTROL represent medications having an influence on the cell proliferation state or the number of autophagosomes.

In an example illustrated in FIG. 9, cell(s) stimulated with a medication A represent that the cell(s) have proliferated and the number of autophagosomes has decreased. In addition, cell(s) stimulated with a medication B represent that the cell(s) have proliferated and the number of autophagosomes has increased. That is, the graph illustrated in FIG. 9 can represent an influence of the medications by using the cell proliferation and the number of autophagosomes. In this way, for example, the medication B can represent a medication having functions to increase the number of autophagosomes and to proliferate the cell(s). In addition, besides the graph illustrated in FIG. 9, whether the medication B induces a selective autophagy or a non-selective autophagy can be represented by examining the state of molecular congestion and the number of autophagosomes.

With reference to FIG. 8 again, the stimulus determination unit 105a acquires the graph from the state determination unit 103a. The stimulus determination unit 105a, on the basis of the graph acquired from the state determination unit 103a, determines whether a stimulus induces or inhibits a selective autophagy or a non-selective autophagy for cell(s), and further determines an influence of the stimulus on a change in the number of the cells (step S250).

The stimulus determination unit 105a determines that the stimulus causing the cell proliferation to tend to increase and causing the number of autophagosomes to decrease is a stimulus restoring survival of cell(s) in which an autophagy cell death occurs. The autophagy cell death refers to death of cell(s) that occurs when autophagic activity becomes excessive. That is, the stimulus determination unit 105a determines that the medication having a plot in the region A illustrated in FIG. 9 is a medication inhibiting autophagy and providing a stimulus promoting cell proliferation.

The stimulus determination unit 105a determines that the stimulus causing the cell proliferation to tend to increase and the number of autophagosomes to increase is a stimulus restoring survival of cell(s), the autophagic activity of which is less than autophagic activity in other cell(s) and the cell proliferation of which is less adversely affected. That is, the stimulus determination unit 105a determines that the medication having a plot in the region B illustrated in FIG. 9 is a medication promoting autophagy and providing a stimulus promoting cell proliferation.

The stimulus determination unit 105a determines that the stimulus causing the cell proliferation to tend to decrease and causing the number of autophagosomes to decrease is a stimulus suppressing a selective autophagy to restrain cell proliferation. That is, the stimulus determination unit 105a determines that the medication having a plot in the region C illustrated in FIG. 9 is a medication inhibiting autophagy and providing a stimulus inhibiting cell proliferation.

The stimulus determination unit 105a determines that the stimulus causing the cell proliferation to tend to decrease and causing the number of autophagosomes to increase is a stimulus promoting autophagy to cause an autophagy cell death. That is, the stimulus determination unit 105a determines that the medication having a plot in the region D illustrated in FIG. 9 is a medication promoting autophagy and providing a stimulus inhibiting cell proliferation.

Note that the interpretation described above of the regions illustrated in FIG. 9 is one interpretation and is not limited to the interpretation described above. For example, the interpretation may differ depending on a cell type that is handled.

The stimulus determination unit 105a feeds the determination result to the result output unit 104a. The result output unit 104a causes the display unit 30 to display the determination result acquired from the stimulus determination unit 105a.

Overview of Second Embodiment

As described above, the image processing device 10a includes the captured image acquisition unit 100a, the autophagosome observation unit 101a, the molecular congestion observation unit 102a, the state determination unit 103a, the stimulus determination unit 105a, and the result output unit 104a. The captured image acquisition unit 100a feeds a cell image and experimental conditions for cell(s) in association with each other to the autophagosome observation unit 101a and the molecular congestion observation unit 102a. In this way, the autophagosome observation unit 101a can count the number of autophagosomes and the number of cells associated with the experimental conditions. In addition, the molecular congestion observation unit 102a can observe the state of molecular congestion associated with the experimental conditions.

In the embodiment, the identification of medications, stimuli, and the like leading to improvement in a pathological condition by autophagic activity control can be achieved. For example, wastes of a protein named A are assumed to be accumulated in certain pathologic cell(s) and adversely affect cell growth. In this case, the identification of a medication selectively removing the protein named A and improving cell growth is demanded. Thus, a medication inducing a selective autophagy is identified based on a correlation between the molecular congestion and the number of autophagosomes after medication treatment. Further, if a medication positively inducing a selective autophagy and improving cell proliferation can be identified based on a correlation between cell proliferation and the number of autophagosomes after medication treatment, the identification of a medication suitable for the pathologic cell(s) can be achieved.

The state determination unit 103a acquires the experimental conditions, the number of autophagosomes, and the number of cells from the autophagosome observation unit 101a. The state determination unit 103a acquires the experimental conditions and the state of molecular congestion from the molecular congestion observation unit 102a. The state determination unit 103a determines, for each of the experimental conditions, the state of autophagic activity on the basis of the acquired number of autophagosomes and the acquired state of molecular congestion. In this way, the image processing device 10a can determine the state of autophagic activity according to the stimulus.

The stimulus determination unit 105a acquires the state of autophagic activity from the state determination unit 103a for each of the experimental conditions. The stimulus determination unit 105a determines whether a medication applying a stimulus to cell(s) induces a selective autophagy or a non-selective autophagy on the basis of a change in autophagic activity, and further determines an influence of the stimulus on a change in the number of the cells. In this way, the image processing device 10a can determine an influence of the medication on the autophagic activity of the cell(s). In addition, the image processing device 10a can determine whether the medication has a relationship with a change in the state of autophagic activity and a change in cell proliferation. That is, the image processing device 10a can examine whether an autophagy-controlling medication has an influence on the autophagic activity of the cell(s).

Note that the state determination unit 103a described above is not necessarily required to perform the processing of plotting a graph, and the state determination unit 103a may generate information in a state where a time-lapse change in the number of autophagosomes, a time-lapse change in the number of cells, and a time-lapse change in the state of molecular congestion are associated with the experimental conditions. The stimulus determination unit 105a may determine whether a stimulus that the cell(s) have received induces a selective autophagy or a non-selective autophagy, on the basis of information in a state where a time-lapse change in the number of autophagosomes and a time-lapse change in the state of molecular congestion are associated with the experimental conditions and may determine an influence of the stimulus on a change in the number of the cells.

Third Embodiment

Next, a configuration of an image processing device configured to identify a molecule involved in autophagy will be described with reference to FIG. 10. Note that the same configurations and operations as those in the first embodiment and the second embodiment will be denoted by the same reference signs and the description of the same configurations and operations will be omitted.

Figure 10:
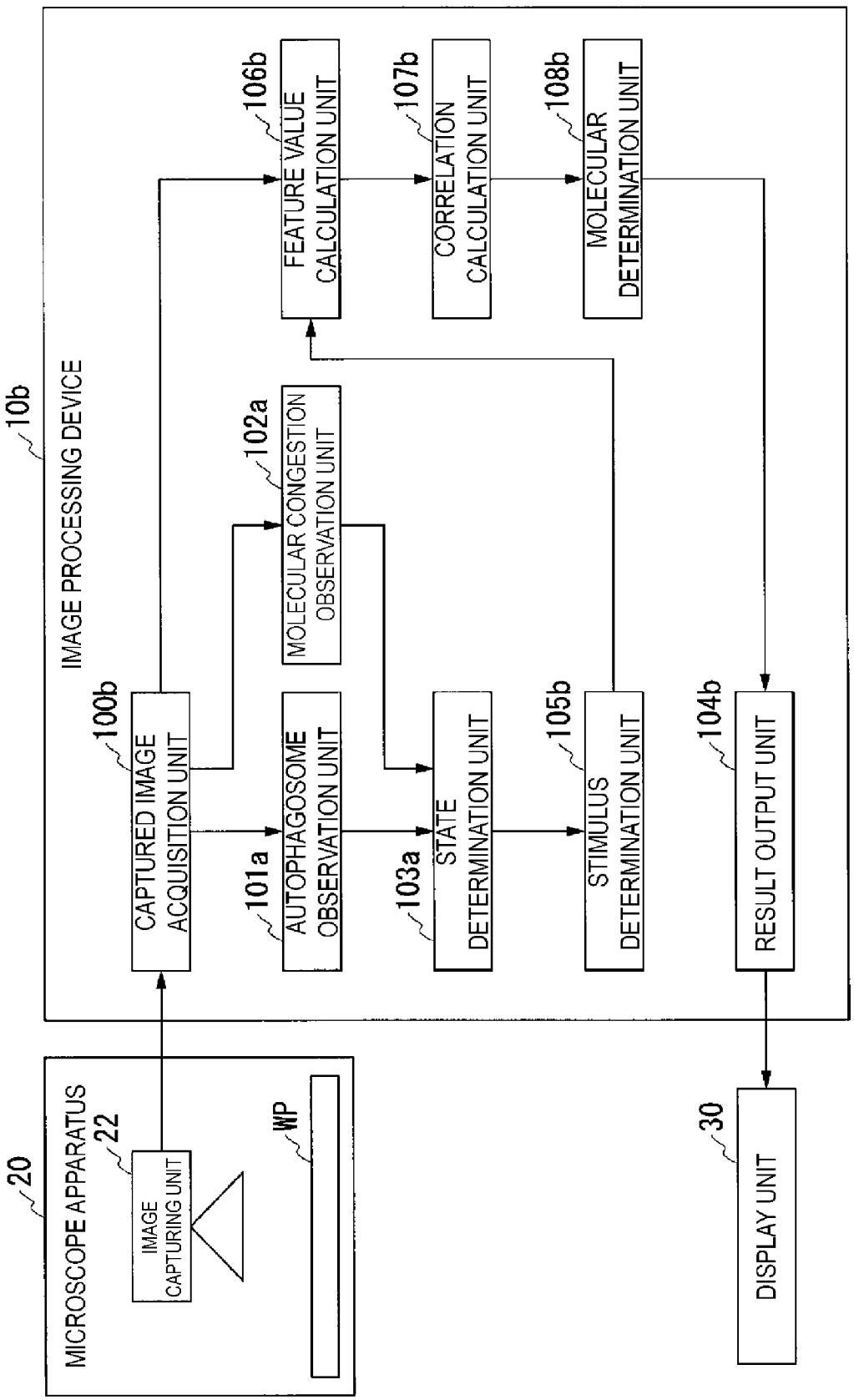
FIG. 10 is a view illustrating an example of a functional configuration of an image processing device configured to identify a molecule involved in autophagy.

FIG. 10 is a view illustrating an example of a functional configuration of an image processing device 10b configured to identify a molecule involved in autophagy. The image processing device 10b identifies a molecule correlating with a change in autophagic activity.

The image processing device 10b includes a captured image acquisition unit 100b, the autophagosome observation unit 101a, the molecular congestion observation unit 102a, the state determination unit 103a, a stimulus determination unit 105b, a feature value calculation unit 106b, a correlation calculation unit 107b, a molecular determination unit 108b, and a result output unit 104b.

The captured image acquisition unit 100b acquires cell images from the image capturing unit 22 in association with experimental conditions. The cell images include cell images in which stimulated cell(s) have been image captured and cell images in which control cell(s) are image captured. The captured image acquisition unit 100b feeds the cell images acquired from the image capturing unit 22, in a state where the cell images are associated with the experimental conditions, to the autophagosome observation unit 101a, the molecular congestion observation unit 102a, and the feature value calculation unit 106b.

The stimulus determination unit 105b feeds the results determined for each of the experimental conditions to the feature value calculation unit 106b.

The feature value calculation unit 106b acquires the cell images in a state where the cell images are associated with the experimental conditions, from the captured image acquisition unit 100b. The feature value calculation unit 106b calculates feature values of subcellular components on the basis of the acquired cell images. The feature values include the brightness of the cell images, cell area of the images, distribution of the brightness of the cell images within the image, a shape, and the like. That is, the feature values include a characteristic derived from information acquired from the captured cell images. That is, the feature values include a characteristic derived from information acquired from the captured cell images. For example, the distribution of the brightness in the acquired images is calculated. Positional information indicative of a change in brightness different from others may be obtained from a change in the distribution of the brightness during a predetermined time or a change associated with a change in a cellular state such as differentiation in the distribution of the brightness that are calculated by using a plurality of images differing in a time series or in a change in a cellular state such as differentiation, and the change in the brightness may be used as the feature values.

In addition, the feature value calculation unit 106b may extract a dynamic feature value, by observing each of the plurality of images captured at an interval of predetermined time, such as cell contraction, a heartbeat cycle, a cell migration rate, a change in the degree of nuclear chromatin aggregation being an indicator of healthy and dying cell(s), a change rate in the number and lengths of processes of neurons, the number of synapses in neurons, neural activity such as a membrane potential change, a change in intracellular calcium concentration, second messenger activity, a morphological change of an organelle, an intracellular behavior of molecules, a nuclear morphology, a behavior of a nuclear structure, and a behavior of DNA molecules. These feature values extraction methods use Fourier transformation, Wavelet transformation, and temporal differentiation, for example, and use a moving average for noise removal.

The feature value calculation unit 106b feeds the calculated feature values to the correlation calculation unit 107b. The correlation calculation unit 107b acquires the feature values from the feature value calculation unit 106b. The correlation calculation unit 107b calculates a correlation between subcellular components on the basis of the acquired feature values. Note that in the following description, the correlation calculated by the correlation calculation unit 107b is also referred to as a network. In this example, the correlation calculation unit 107b calculates a network by the Graphical Lasso method. The Graphical Lasso method is an efficient algorithm for estimating an accuracy matrix from a L1-normalized Gaussian model. For example, refer to "Sparse inverse covariance estimation with the graphical lasso" in Biostatistics (2008), 9, 3 432-441, authored by JEROME FRIEDMAN, TREVOR HASTIE, and ROBERT TIBSHIRANI. Note that the correlation calculation unit 107b may calculate the network by a method other than the Graphical Lasso method.

The correlation calculation unit 107b calculates the network calculated on the basis of the captured cell images in which the stimulated cell(s) have been image captured and a network calculated on the basis of the cell images in which the control cell(s) is image captured. In the following description, the network calculated on the basis of the cell images in which the stimulated cell(s) has been image captured is referred to as a stimulus network. In addition, in the following description, the network calculated on the basis of the cell images in which the control cell(s) is image captured is referred to as a control network. The correlation calculation unit 107b feeds the calculated stimulus network and the calculated control network to the molecular determination unit 108b.

A network that the correlation calculation unit 107b calculates will be described here. The network includes nodes, edges, and the like. The network is represented by an edge connecting the nodes to each other. The node is a subcellular component in this example. Accordingly, a correlation existing between the feature values of the subcellular components of the cell(s) is represented by an edge existing between the feature values of the subcellular components. In the embodiment, a correlation existing between the feature values of the subcellular components is represented by an edge connecting the subcellular components to each other. It goes without saying that a correlation existing between the feature values of the subcellular components is represented by an edge connecting the feature values of the subcellular components to each other.

The molecular determination unit 108b acquires a stimulus network and a control network from the correlation calculation unit 107b. The molecular determination unit 108b performs a comparison of the stimulus network with the control network and determines a molecule involved in the autophagy induced by the stimulus determined by the stimulus determination unit 105b. The molecular determination unit 108b feeds the determination result to the result output unit 104b.

The result output unit 104b acquires the determination result from the molecular determination unit 108b and causes the display unit 30 to display the determination result.

Example of Processing of Image Processing Device According to Third Embodiment

Next, with reference to FIG. 11, an example of processing in which the image processing device 10b determines a molecule involved in an autophagy induced by a stimulus will be described.

Figure 11:
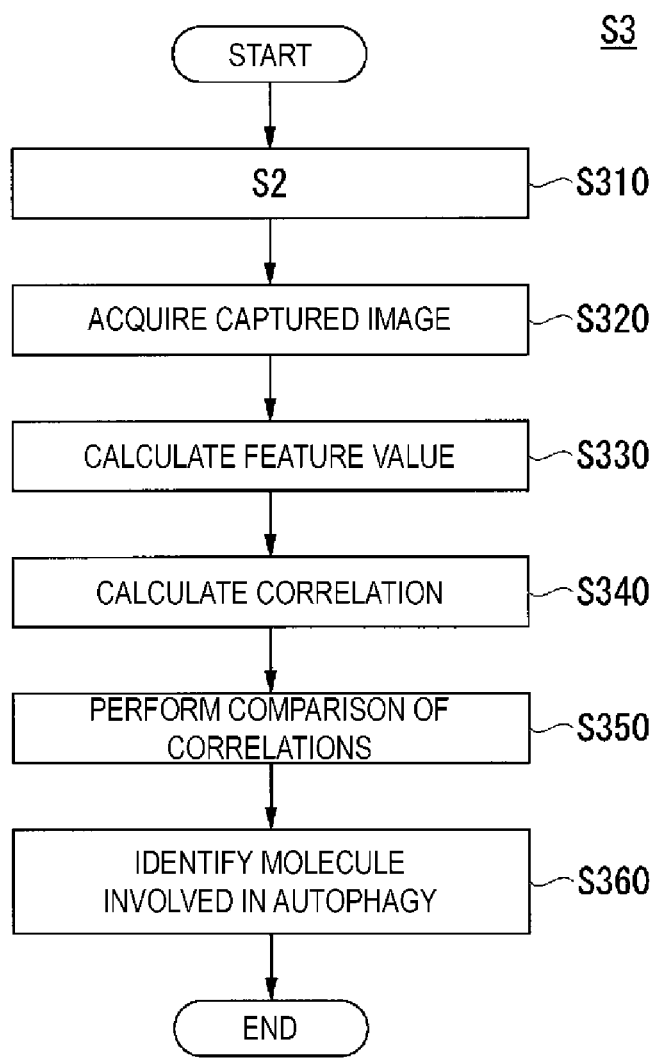
FIG. 11 is a flowchart illustrating an example of processing in which an image processing device according to a third embodiment determines a molecule involved in an autophagy induced by a stimulus.

FIG. 11 is a flowchart illustrating an example of processing in which the image processing device 10b according to the third embodiment determines a molecule involved in an autophagy induced by a stimulus. The image processing device 10b according to the third embodiment determines a molecule having a correlation with a change in autophagic activity induced by a stimulus. Note that the processing procedure described here is an example, and a processing procedure may be omitted, or another processing procedure may be added.

The image processing device 10b performs processing S2 illustrated in FIG. 8 to determine whether the stimulus applied to cell(s), a state of the autophagic activity, is a selective autophagy or a non-selective autophagy (step S310). The captured image acquisition unit 100b acquires the cell images from a microscope apparatus 20 together with the experimental conditions for the cell(s) (step S320). The captured image acquisition unit 100b feeds the cell images acquired from the microscope apparatus 20 and the experimental conditions in association with each other to the feature value calculation unit 106b. The feature value calculation unit 106b acquires the cell images associated with the experimental conditions from the captured image acquisition unit 100b. The feature value calculation unit 106b calculates the feature value for each of the experimental conditions (step S330). The feature value calculation unit 106b feeds the calculated feature value and the experimental conditions in association with each other to the correlation calculation unit 107b. The correlation calculation unit 107b acquires the feature values associated with the experimental conditions from the feature value calculation unit 106b. The correlation calculation unit 107b calculates a stimulus network and a control network on the basis of the acquired feature values (step S340). The correlation calculation unit 107b feeds the calculated stimulus network and the calculated control network to the molecular determination unit 108b. The molecular determination unit 108b acquires the stimulus network and the control network from the correlation calculation unit 107b. The molecular determination unit 108b performs a comparison of the acquired stimulus network with the acquired control network (step S350). The molecular determination unit 108b determines, as a target molecule, a molecule having a difference between the edges present in the stimulus network and between the edges present in the control network (step S360). The target molecule is a molecule correlating with the autophagic activity induced by a stimulus. The target molecule is a molecule involved in autophagy induced in cell(s).

Figure 12A:
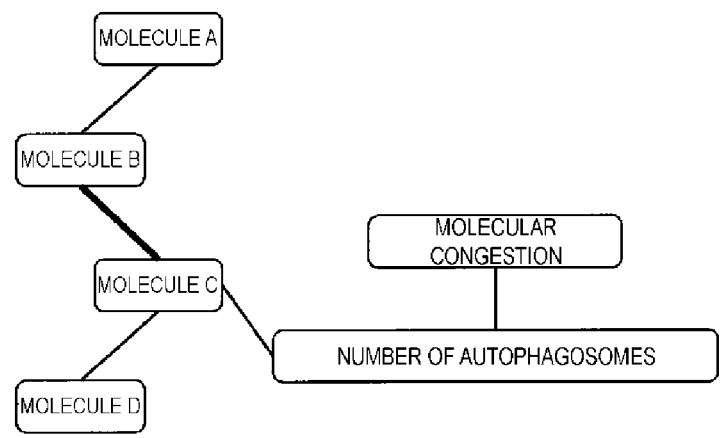
FIGS. 12A and 12B are views illustrating an example of a stimulus network and a control network calculated by a correlation calculation unit.
Figure 12B:
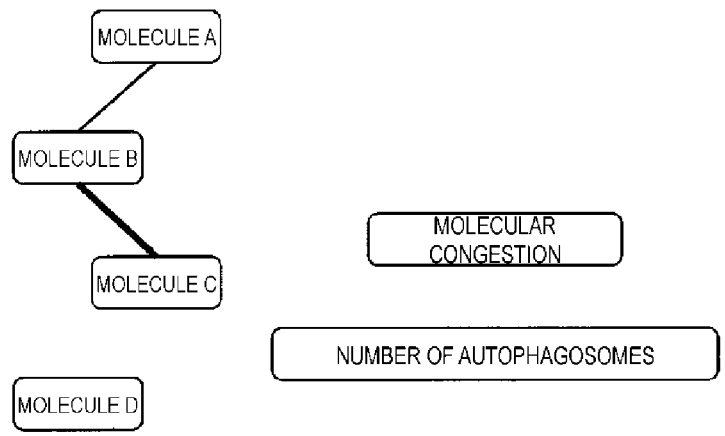

With reference to FIGS. 12A and 12B, an example of the stimulus network and the control network will be described here.

FIGS. 12A and 12B are views illustrating an example of a stimulus network and a control network calculated by the correlation calculation unit 107b.

FIG. 12A is an example of the stimulus network. FIG. 12B is an example of the control network. Molecules A, B, C, and D, and the number of autophagosomes, and molecular congestion that are present in the network illustrated in each of FIGS. 12A and 12B are examples of the node. The molecules A, B, C, and D are feature values that can be identified from the cell images. The feature values include a brightness value of a pixel, an area of a certain region present in an image, a distribution value of brightness of a pixel, and the like. Accordingly, for example, the feature value of the molecule A includes a brightness value of a pixel corresponding to the molecule A. The molecule identified from the cell image includes DNAs, proteins, metabolites, and the like. As illustrated in FIG. 12A, an edge connecting the molecules A and B indicates a correlation existing between the molecules A and B. The edge connecting the molecules A and B indicates a correlation existing between the feature values of the molecules A and B. Similarly, an edge connecting the molecules B and C indicates a correlation existing between the molecules B and C. In addition, a correlation also exists between the molecule C and the number of autophagosomes. In this case, for example, a change in a brightness value of the molecule C correlates with an increase and a decrease in the number of autophagosomes.

Figure 13:
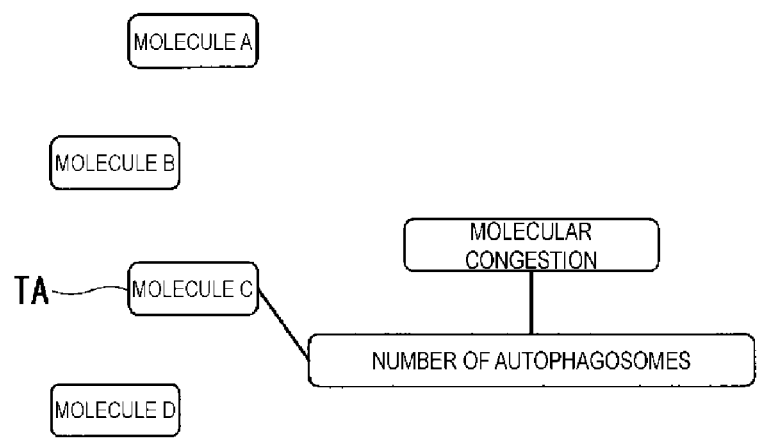
FIG. 13 is a view illustrating an example of a result of a molecular determination unit comparing a stimulus network with a control network.

Next, with reference to FIG. 13, there is illustrated a result of comparison by the molecular determination unit 108b between the stimulus network and the control network illustrated in FIGS. 12A and 12B.

FIG. 13 is a view illustrating an example of a result of the molecular determination unit 108b comparing the stimulus network with the control network.

The molecular determination unit 108b performs a comparison of the stimulus network illustrated in FIG. 12A with the control network illustrated in FIG. 12B to calculate a network illustrated in FIG. 13. Specifically, the molecular determination unit 108b calculates the difference between the edges in the stimulus network and the control network. In this example, as illustrated in FIG. 13, a difference exists in the edge between the molecule C and the number of autophagosomes and in the edge between the number of autophagosomes and the molecular congestion. The molecular determination unit 108b determines that the intracellular molecule C involved in the autophagic activity induced by a stimulus is a target molecule TA. In other words, the molecular determination unit 108b determines that the autophagic activity induced by a stimulus provided by a medication has a correlation with the molecule C. Note that in FIG. 12A, although an edge existing between the molecule C and the number of autophagosomes indicates a correlation existing between the molecule C and the autophagic activity, the molecule C and the autophagic activity may be determined to be correlated with each other even in a case where an edge exists between the molecule C and the molecular congestion.

Note that, although in the following description, the correlation calculation unit 107b calculates the network by using the number of autophagosomes and the state of molecular congestion as the feature values, the feature values may not include the number of autophagosomes and the state of molecular congestion.

Overview of Third Embodiment

As described above, the image processing device 10b includes the feature value calculation unit 106b, the correlation calculation unit 107b, and the molecular determination unit 108b. The feature value calculation unit 106b calculates feature values on the basis of a cell image. The correlation calculation unit 107b calculates a network on the basis of the feature values calculated by the feature value calculation unit 106b. In this way, the image processing device 10b can calculate a correlation between the feature values present in the cell image. The image processing device 10b can calculate a correlation between the feature values to determine a molecule correlating with autophagic activity induced by a stimulus determined by the stimulus determination unit 105b.

The molecular determination unit 108b determines, on the basis of the stimulus network and the control network calculated by the correlation calculation unit 107b, a molecule involved in autophagic activity induced by a stimulus determined by the stimulus determination unit 105b. In this way, the image processing device 10b can determine a molecule involved in an autophagy induced by a medication.

Note that the image processing device 10b may be an analysis device configured to analyze a correlation between the feature values in cell(s) due to a stimulus. In this case, the captured image acquisition unit 100b provided in the analysis device acquires a plurality of cell images in which cell(s) having not received a stimulus or stimulated cell(s) is image captured. The feature value calculation unit 106b provided in the analysis device calculates the feature values of subcellular components on the basis of information about the plurality of cell images acquired by the captured image acquisition unit 100b. The correlation calculation unit 107b provided in the analysis device estimates functions of the subcellular components. In this example, the feature value calculation unit 106b calculates each of the number of autophagosomes, the state of molecular congestion, and the molecule present in the cell(s) as a feature value to estimate the functions of the subcellular components. The analysis device calculates a correlation between the functions of the subcellular components and the feature values of the subcellular components constituting the cell(s). Specifically, the analysis device calculates a correlation relationship on the basis of the number of autophagosomes calculated on the basis of the cell(s) image captured in the cell images and the state of molecular congestion. The analysis device analyzes whether a selective autophagy or a non-selective autophagy in the cell(s) image captured in the cell images has been promoted or inhibited by a provided stimulus.

Note that the analysis device calculates a type of autophagy on the basis of the number of autophagosomes and the state of molecular congestion calculated on the basis of the cell(s) image captured in the cell images. A correlation between the calculated type of autophagy and the feature values of the subcellular components constituting the cell(s) may be calculated. That is, the analysis device calculates a correlation of the functions of the cell(s) with the feature values of the subcellular components constituting the cell(s) and can analyze a correlation of the functions of the cell(s) induced by a stimulus given to the cell(s) image captured in the cell images with the subcellular components involved in the induction of the functions of the cell(s).

Note that the nodes are not limited to the examples described above and for example, include a plurality of types in accordance with the subcellular components. As an example, a feature value of an image of a cell nucleus includes a total brightness value within the nucleus, the area of the nucleus, and the like. A feature value of an image of cytoplasm includes a total brightness value within the cytoplasm, the area of the cytoplasm, and the like. In addition, a feature value of an image of the whole cell includes a total brightness value within the cell, the area of the cell, and the like. In addition, a feature value of an image of a mitochondrion includes a fragmentation rate.

In addition, the feature value calculation unit 106b may calculate the feature values on the basis of information about the experimental conditions for cell(s) associated with a cell image. For example, in the case of a cell image captured when an antibody is caused to react with cell(s), the feature value calculation unit 106b may calculate, in the case of the captured cell image, a feature value specific to the case where an antibody is caused to react with cell(s). In addition, in the case of a cell image captured when cell(s) are stained or a fluorescence protein is applied to cell(s), the feature value calculation unit 106b may calculate a feature value specific to the case where cell(s) is stained or a fluorescence protein is applied to cell(s).

Fourth Embodiment

Next, a configuration in which an image processing device identifies a molecule involved in autophagic activity on the basis of a result of omics analysis by another analysis device will be described with reference to FIG. 14. Note that the same configurations and operations as those in the first embodiment, the second embodiment, and the third embodiment are denoted by the same reference signs, and the description of the same configurations and operations will be omitted.

Figure 14:
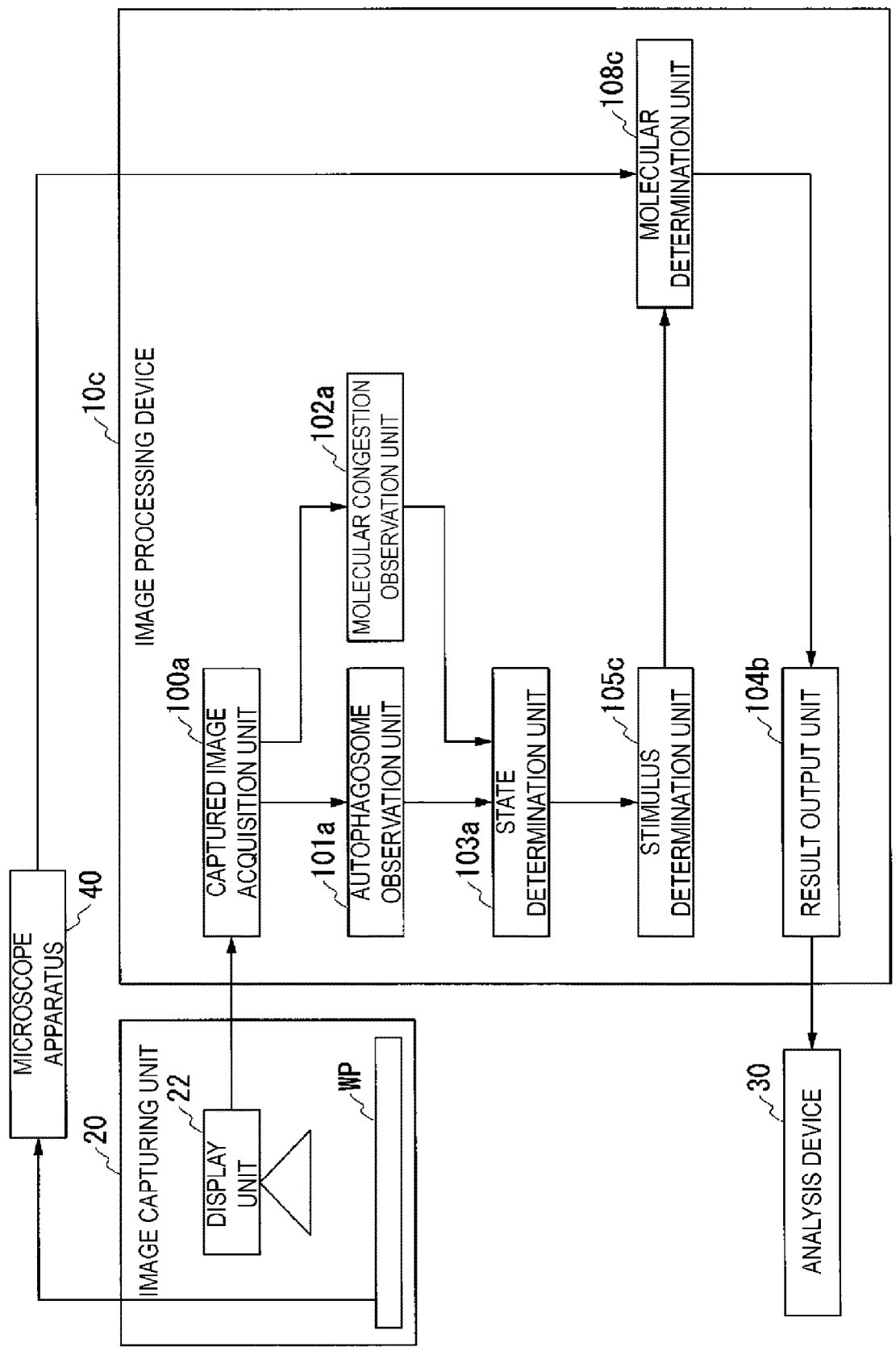
FIG. 14 is a view illustrating an example of a functional configuration of an image processing device.

FIG. 14 is a view illustrating an example of a functional configuration of an image processing device 10c.

The image processing device 100c includes the captured image acquisition unit 100a, the autophagosome observation unit 101a, the molecular congestion observation unit 102a, the state determination unit 103a, a stimulus determination unit 105c, a molecular determination unit 108c, and the result output unit 104b.

The stimulus determination unit 105c, on the basis of a change in a state of autophagic activity determined by the state determination unit 103a, determines whether a stimulus applied to cell(s) has induced a selective autophagy or a non-selective autophagy. The stimulus determination unit 105c outputs the determination result to the molecular determination unit 108c.

The molecular determination unit 108c acquires the result of omics analysis from an analysis device 40. The analysis device 40 performs omics analysis on cell(s). The omics analysis is an exhaustive analysis on cell(s). Specifically, the omics analysis is the exhaustive analysis on nucleic acids, DNAs, RNAs, proteins, low molecule metabolites, lipids, metabolites, and sugar chains that are present in cell(s). The omics analysis on cell(s) is performed by using an analysis device such as a high-density microarray and scanner, a high-speed sequencer, and a mass spectrometer. Note that the cell(s) to be analyzed by the analysis device 40 are not limited to cell(s) cultured in the well plate WP and image captured as cell images but may be cell(s) having received the same stimulus as a stimulus for the image captured cell(s). A case where the analysis device 40 outputs the network illustrated in each of FIGS. 12A and 12B as a result of the omics analysis will be described, but the analysis device 40 is not limited to this case.

The analysis device 40 feeds the analysis result to the molecular determination unit 108c. The molecular determination unit 108c acquires the result of the omics analysis from the analysis device 40. The molecular determination unit 108c acquires a state of autophagic activity induced by a stimulus from the stimulus determination unit 105c. The molecular determination unit 108c determines a molecule involved in the autophagic activity on the basis of the state of autophagic activity and the result of the omics analysis.

The molecular determination unit 108c outputs the determination result to the result output unit 104b. The result output unit 104b causes the display unit 30 to display the acquired determination result.

Example of Processing of Image Processing Device According to Fourth Embodiment

Next, with reference to FIG. 15, an example of processing in which the image processing device 10c determines a molecule involved in an autophagy induced by a stimulus on the basis of the result of the omics analysis will be described.

Figure 15:
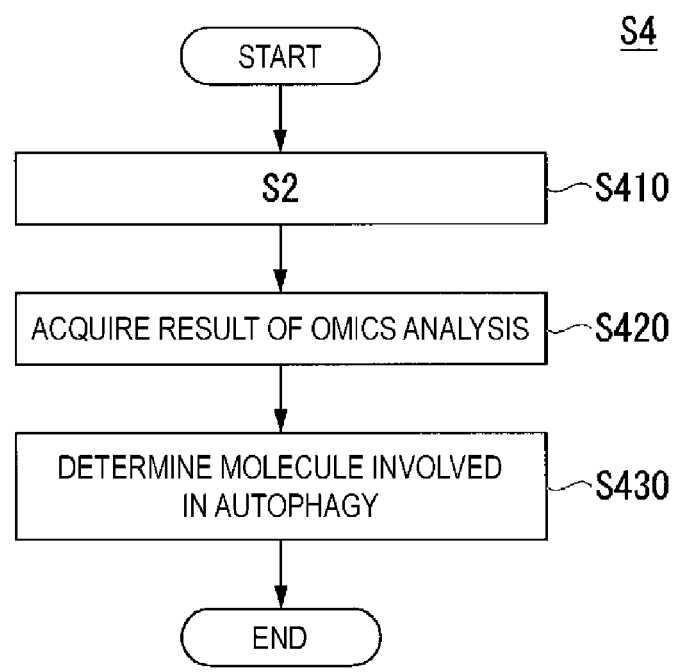
FIG. 15 is a flowchart illustrating an example of processing in which an image processing device according to a fourth embodiment determines a molecule involved in an autophagy induced by a stimulus.

FIG. 15 is a flowchart illustrating an example of processing in which the image processing device 10c according to the fourth embodiment determines a molecule involved in the autophagy induced by a stimulus. Note that the processing procedure described here is an example, and a processing procedure may be omitted, or another processing procedure may be added.

The image processing device 10c performs processing S2 illustrated in FIG. 8 to determine whether a stimulus applied to cell(s) has induced a selective autophagy or a non-selective autophagy (step S410). The analysis device 40 performs the omics analysis on each of the stimulated cell(s) and control cell(s). The analysis device 40 feeds a network calculated on the basis of the omics analysis to the molecular determination unit 108c. The molecular determination unit 108c acquires the determination result of whether the stimulus has induced a selective autophagy or a non-selective autophagy. The molecular determination unit 108c acquires a network calculated by using the omics analysis from the analysis device 40 (step S420).

The molecular determination unit 108c determines a molecule involved in the autophagic activity on the basis of the result of the omics analysis (step S430). The molecular determination unit 108c identifies a molecule involved in the autophagic activity by performing a comparison of a network calculated on the basis of the stimulated cell(s) with a network calculated on the basis of the control cell(s). Note that the molecular determination unit 108c may identify the molecule on the basis of information other than the network calculated by the analysis device 40. The analysis device 40, in the case of analyzing a state of molecules present in the cell(s) by using the omics analysis, may identify a molecule involved in the autophagic activity by performing a comparison of a state of molecules present in the stimulated cell(s) with a state of molecules present in the control cell(s).

Overview of Fourth Embodiment

As described above, the image processing device 10c includes the stimulus determination unit 105c and the molecular determination unit 108c. The molecular determination unit 108c acquires a result of omics analysis on cell(s) from the analysis device 40. The molecular determination unit 108c acquires a determination result of whether a stimulus applied to the cell(s) has induced or inhibited a selective autophagy or a non-selective autophagy from the stimulus determination unit 105c. The molecular determination unit 108c identifies a molecule involved in autophagy on the basis of the result of the omics analysis and the determination result of whether a stimulus applied to the cell has induced or inhibited a selective autophagy or a non-selective autophagy. In this way, the image processing device 10c can identify a molecule involved in autophagy on the basis of the results analyzed by using omics analysis.

Note that in the embodiments described above, the type of autophagy is identified on the basis of the information about the autophagy and the information about the congestion of molecules from the image including the cell(s), but information other than the image including the cell(s) may be used. For example, Western blotting may be used in place of the image including the cell(s). It goes without saying that information about, for example, Western blotting may be used, as another technique, together with the image including the cell(s).

Example of Determination Result Display Device

A display device configured to display the determination results by the image processing device according to each of the first to fourth embodiments described above will be described. The display device acquires the determination results by the image processing device. The display device causes the display unit 30 to display the acquired determination results.

Note that the display device may cause the display unit 30 to display the determination results by the image processing device by a modified method of displaying the acquired determination results. For example, in a case where the image processing device outputs the determination results illustrated in FIG. 9 as data for coordinates obtained before plotting on the graph, the display device may generate image data obtained after plotting on the graph and cause the display unit 30 to display the image data. That is, the display device may have at least some of the functions of the image processing device according to any of the above-described embodiments in addition to the display unit 30.

The display device acquires the determination results by the image processing device. The display device causes the display unit 30 to display an image on the basis of the acquired determination results. In this way, the display device can present the determination results by the image processing device to a user using the image processing device. In addition, the display device can present a display image easily recognizable by a user by a modified method of displaying the determination results by the image processing device.

Note that the above-described various kinds of processing may be performed by recording a program for executing the processing of the image processing device 10, the image processing device 10a, the image processing device 10b, the image processing device 10c, the analysis device, and the display device in the embodiments of the present invention in a recording medium that can be read by a computer and by causing a computer system to read and execute the program recorded in the recording medium.

Note that the "computer system" here referred to a computer system including an OS and hardware such as a peripheral device. In addition, when the "computer system" uses a WWW system, the computer system also includes a homepage provision environment (or a display environment). In addition, a "recording medium that can be read by a computer" refers to a writable non-volatile memory such as a flexible disk, a magneto-optical disk, a ROM, or a flash memory, a portable recording medium such as a CD-ROM, or a storage device such as a hard disk built into the computer system.

Further, the "recording medium that can be read by a computer" may also include a medium holding a program for a certain period of time, such as a volatile memory (a Dynamic Random Access Memory (DRAM), for example) built into a computer system serving as a server or a client when the program is transmitted over a network such as the Internet or a communication circuit such as a telephone circuit. In addition, the above-described program may be transmitted from the computer system in which the program is stored in a storage device or the like, to another computer system, via a transmission medium or by a transmission wave in the transmission medium. Here, the "transmission medium" via which the program is transmitted refers to a medium having a function to transmit information is a network such as the Internet (communication network) or a communication circuit such as a telephone circuit (communication line). In addition, the above-described program may be a program for realizing a portion of the above-described functions. Further, the above-described program may be a so-called differential file (differential program) that can realize the above-described functions by a combination with a program having already recorded in the computer system.

The embodiments of the present invention are described above in detail with reference to the drawings, but a specific configuration is not limited to the embodiments, and designs and the like within the scope of the present invention are included.

Note that various aspects of the embodiments described above can be combined as appropriate. In addition, some of the component parts may be removed. In addition, to the extent permissible by law, all publications and US patent documents related to the devices or the like used in the embodiments and the modification examples as described above are incorporated herein by reference.

REFERENCE SIGNS LIST

1 Microscope observation system
10, 10a, 10b, 10c Image processing device
20 Microscope apparatus
30 Display unit
40 Analysis device
100, 100a, 100b Captured image acquisition unit
101, 101a Autophagosome observation unit
102, 102a Molecular congestion observation unit
103, 103a State determination unit
104, 104a, 104b Result output unit
105a, 105b, 105c Stimulus determination unit
106b Feature value calculation unit
107b Correlation calculation unit
108b, 108c Molecular determination unit

The invention claimed is:

1. An image processing device comprising
a processor that executes a program stored in a memory so as to be configured to determine a type of autophagy induced in a cell, (i) based on information indicative of autophagic activity in the cell, which is present in a cell image in which the cell is image captured, and (ii) based on information indicative of congestion of molecules in the cell present in the cell image.

2. The image processing device according to claim 1, wherein
the type of autophagy induced in the cell includes a selective autophagy and a non-selective autophagy, and
the processor determines whether the autophagy induced in the cell is the selective autophagy or the non-selective autophagy, (i) based on information indicative of a degree of autophagic activity in the cell present in the cell image and (ii) based on information indicative of a degree of congestion of molecules in the cell.

3. The image processing device according to claim 2, wherein
the cell includes a stimulated cell, and
the processor is configured to determine whether a stimulus induces the selective autophagy or the non-selective autophagy, based on the determination.

4. The image processing device according to claim 1, wherein the processor is configured to acquire the cell image in which the cell is image captured.

5. The image processing device according to claim 4, wherein
the cell includes a stimulated cell, and
the processor:
acquires a plurality of cell images in which the stimulated cell is image captured;
is configured to calculate feature values of subcellular components, based on an acquired cell image; and
is configured to calculate a correlation between the feature values of the subcellular components.

6. The image processing device of claim 5, wherein
the processor is configured to perform a comparison of (i) a correlation between feature values of subcellular components calculated based on a cell image of the stimulated cell with (ii) a correlation between feature values of subcellular components calculated based on a cell image of the cell having not received a stimulus.

7. The image processing device according to claim 6, wherein
the processor is configured to identify a molecule involved in the autophagy by using a result of the comparison.

8. The image processing device according to claim 7, wherein
a feature value of a subcellular component includes a degree of activity of the autophagy and a degree of congestion of the molecules, and
the processor calculates a correlation including a degree of activity of the autophagy and a degree of congestion of the molecules.

9. The image processing device according to claim 8, wherein
the processor identifies a molecule involved in the autophagy, based on the correlation including the degree of activity of the autophagy and the degree of congestion of the molecules.

10. The image processing device according to claim 2, wherein
the degree of autophagic activity includes a number of autophagosomes.

11. The image processing device according to claim 2, wherein
the degree of congestion of the molecules includes molecular congestion.

12. The image processing device according to claim 2, wherein
the information indicative of the degree of autophagic activity and/or the information indicative of the congestion of molecules in the cell is analyzed based on information different from the cell image, and the analyzed result is further used to determine whether the selective autophagy or the non-selective autophagy is applicable.

13. The image processing device according to claim 1, further comprising
a display configured to display a result of the determination.

14. An image processing method comprising
utilizing the image processing device of claim 1, determining a type of autophagy induced in a cell, (i) based on information indicative of autophagic activity in the cell, which is present in a cell image in which the cell is image captured, and (ii) based on information indicative of congestion of molecules in the cell present in the cell image.

15. A non-transitory computer-readable medium storing an image processing program causing the image processing device of claim 1 to execute
a determination of a type of autophagy induced in a cell, (i) based on information indicative of autophagic activity in the cell, which is present in a cell image in which the cell is image captured, and (ii) based on information indicative of congestion of molecules in the cell present in the cell image.

16. A system comprising:
the image processing device of claim 1; and
a display configured to display a determination result of the processor of the image processing device.

* * * * *